United States Patent
Baker et al.

(10) Patent No.: US 6,228,082 B1
(45) Date of Patent: May 8, 2001

(54) SYSTEMS AND METHODS FOR ELECTROSURGICAL TREATMENT OF VASCULAR DISORDERS

(75) Inventors: Michael A. Baker, Woodside; Stephen M. Brunell, Mountain View; Ronald A. Underwood, Belmont, all of CA (US)

(73) Assignee: ArthroCare Corporation, Sunnyvale, CA (US)

( * ) Notice: Subject to any disclaimer, the term of this patent is extended or adjusted under 35 U.S.C. 154(b) by 0 days.

(21) Appl. No.: 09/205,640

(22) Filed: Dec. 3, 1998

Related U.S. Application Data

(63) Continuation-in-part of application No. 08/977,845, filed on Nov. 25, 1997, which is a continuation-in-part of application No. 08/562,332, filed on Nov. 22, 1995, now Pat. No. 6,024,733.

(51) Int. Cl.⁷ .................................... A61B 18/14

(52) U.S. Cl. ................................ 606/49; 606/41; 606/50

(58) Field of Search .................... 606/41, 49, 50

(56) References Cited

U.S. PATENT DOCUMENTS

| | | |
|---|---|---|
| 2,050,904 | 8/1936 | Trice . |
| 3,301,258 * | 1/1967 | Werner et al. .......................... 606/50 |
| 4,033,351 | 7/1977 | Hetzel ................................. 128/303 |
| 4,040,426 | 8/1977 | Morrison, Jr. ........................ 128/303 |
| 4,043,342 | 8/1977 | Morrison, Jr. ........................ 128/303 |
| 4,116,198 | 9/1978 | Roos ................................... 128/303 |
| 4,184,492 | 1/1980 | Meinke et al. ....................... 128/303 |
| 4,202,337 | 5/1980 | Hren et al. ........................... 128/303 |
| 4,228,800 | 10/1980 | Degler, Jr. et al. ................. 128/303 |
| 4,248,231 | 2/1981 | Herczog et al. ..................... 128/303 |

(List continued on next page.)

FOREIGN PATENT DOCUMENTS

| | | | |
|---|---|---|---|
| 44 25 015 | 1/1996 | (DE) | ............................ A61B/17/39 |
| 480639 * | 4/1992 | (EP) | ....................................... 606/49 |
| 515 867 | 12/1992 | (EP) | ............................ A61B/17/36 |

(List continued on next page.)

OTHER PUBLICATIONS

Buchelt, M. et al. "Excimer Laser Ablation of Fibrocartilage: An In Vitro and In Vivo Study," (1991) Lasers in Surgery and Medicine 11:271–279.

Costello, A. J. et al. "Nd:YAG Laser Ablation of the Prostate as a Treatment of Benign Prostatic Hypertrophy," (1992) Lasers in Surgery and Medicine 12:121–124.

P.C. Nardella (1989) *SPIE* 1068:42–49 Radio Frequency Energy and Impedance Feedback.

(List continued on next page.)

*Primary Examiner*—Lee Cohen
(74) *Attorney, Agent, or Firm*—John T. Raffle

(57) ABSTRACT

Systems and methods are provided for treating a discolored blood vessel in tissue under the surface of the skin. In this method, one or more active electrode(s) are positioned in close proximity to a target region of the blood vessel, and a sufficient high frequency voltage is applied to the electrode terminal(s) to cause thermal damage to a target region within the blood vessel. The thermal injury causes the vessel to shrink or to thrombose and collapse so that blood flow through the vessel is restricted or completely interrupted. Preferably, the vessel is injured with minimal thermal energy being applied to the surrounding tissue, which prevents the tissue discoloration or scarring associated with prior art thermal processes. The electrode terminal(s) may be positioned on the external surface of the skin, or they may be introduced through a percutaneous penetration in the outer skin surface to the blood vessel. In the latter embodiment, the percutaneous penetration may be formed by advancing one or more needle electrodes through the outer surface of the skin to the target region of the vessel.

17 Claims, 24 Drawing Sheets

U.S. PATENT DOCUMENTS

| | | | |
|---|---|---|---|
| 4,326,529 | 4/1982 | Doss | 128/303.1 |
| 4,381,007 | 4/1983 | Doss | 128/303.1 |
| 4,476,862 | 10/1984 | Pao | 128/303.17 |
| 4,532,924 | 8/1985 | Auth et al. | 128/303 |
| 4,548,207 | 10/1985 | Reimels | 128/303 |
| 4,567,890 | 2/1986 | Ohta et al. | 128/303.13 |
| 4,593,691 | 6/1986 | Lindstrom et al. | 128/303.14 |
| 4,658,817 | 4/1987 | Hardy | 128/303 |
| 4,674,499 | 6/1987 | Pao | 128/303 |
| 4,682,596 | 7/1987 | Bales et al. | 128/303 |
| 4,706,667 | 11/1987 | Roos | 128/303 |
| 4,736,743 | 4/1988 | Daikuzono | 128/303.1 |
| 4,737,678 | 4/1988 | Hasegawa | 313/36 |
| 4,762,128 | 8/1988 | Rosenbluth | 128/343 |
| 4,765,331 | 8/1988 | Petruzzi et al. | 128/303 |
| 4,785,806 | 11/1988 | Deckelbaum | 128/303.1 |
| 4,799,480 | 1/1989 | Abraham et al. | 128/303 |
| 4,823,791 | 4/1989 | D'amelio | 123/303 |
| 4,860,752 | 8/1989 | Turner | 128/422 |
| 4,931,047 | 6/1990 | Broadwin et al. | 604/22 |
| 4,936,301 | 6/1990 | Rexroth et al. | 606/45 |
| 4,943,290 | 7/1990 | Rexroth et al. | 606/45 |
| 4,955,377 | 9/1990 | Lennox et al. | 128/401 |
| 4,967,765 | 11/1990 | Turner et al. | 128/785 |
| 4,968,314 | 11/1990 | Michaels | 606/7 |
| 4,976,711 | 12/1990 | Parins et al. | 606/48 |
| 4,979,948 | 12/1990 | Geddes et al. | 606/33 |
| 4,998,933 | 3/1991 | Eggers et al. | 606/41 |
| 5,007,437 | 4/1991 | Sterzer | 428/786 |
| 5,007,908 | 4/1991 | Rydell | 606/47 |
| 5,009,656 | 4/1991 | Reimels | 606/48 |
| 5,035,696 | 7/1991 | Rydell | 606/47 |
| 5,037,421 | 8/1991 | Boutacoff et al. | 606/15 |
| 5,057,105 | 10/1991 | Malone et al. | 606/28 |
| 5,057,106 | 10/1991 | Kasevich et al. | 606/33 |
| 5,059,192 | 10/1991 | Zaias | 606/9 |
| 5,061,266 | 10/1991 | Hakky | 606/15 |
| 5,065,515 | 11/1991 | Iderosa | 30/140 |
| 5,078,717 | 1/1992 | Parins et al. | 606/48 |
| 5,080,660 | 1/1992 | Buelna | 606/48 |
| 5,083,565 | 1/1992 | Parins | 128/642 |
| 5,098,431 | 3/1992 | Rydell | 606/48 |
| 5,102,410 | 4/1992 | Dressel | 606/15 |
| 5,108,391 | 4/1992 | Flachenecker et al. | 606/38 |
| 5,112,330 | 5/1992 | Nishigaki et al. | 606/46 |
| 5,122,138 | 6/1992 | Manwaring | 606/46 |
| 5,125,928 | 6/1992 | Parins et al. | 606/48 |
| 5,143,063 | 9/1992 | Fellner | 128/399 |
| 5,147,354 | 9/1992 | Boutacoff et al. | 606/15 |
| 5,178,620 | 1/1993 | Eggers et al. | 606/41 |
| 5,182,857 | 2/1993 | Simon | 30/34 |
| 5,190,517 | 3/1993 | Zieve et al. | 604/22 |
| 5,192,280 | 3/1993 | Parins | 606/48 |
| 5,195,959 | 3/1993 | Smith | 604/34 |
| 5,197,963 | 3/1993 | Parins | 606/46 |
| 5,217,455 | 6/1993 | Tan | 606/9 |
| 5,217,457 | 6/1993 | Delahuerga et al. | 606/42 |
| 5,226,907 | 7/1993 | Tankovich | 606/133 |
| 5,231,984 | 8/1993 | Santana-Blank | 128/395 |
| 5,241,972 | 9/1993 | Bonati | 128/898 |
| 5,249,585 | 10/1993 | Turner et al. | 607/99 |
| 5,261,410 | 11/1993 | Alfano et al. | 128/664 |
| 5,267,994 | 12/1993 | Gentelia et al. | 606/15 |
| 5,267,997 | 12/1993 | Farin et al. | 606/38 |
| 5,273,524 | 12/1993 | Fox et al. | 604/21 |
| 5,277,201 | 1/1994 | Stern | 607/98 |
| 5,281,216 | 1/1994 | Klicek | 606/42 |
| 5,281,218 | 1/1994 | Imran | 606/41 |
| 5,287,380 | 2/1994 | Hsia | 372/69 |
| 5,290,273 | 3/1994 | Tan | 606/9 |
| 5,290,282 | 3/1994 | Casscells | 606/29 |
| 5,300,069 | 4/1994 | Hunsberger et al. | 606/37 |
| 5,300,099 | 4/1994 | Rudie | 607/101 |
| 5,301,687 | 4/1994 | Wong et al. | 607/116 |
| 5,304,169 | 4/1994 | Sand | 606/5 |
| 5,304,170 | 4/1994 | Green | 606/9 |
| 5,312,395 | 5/1994 | Tan et al. | 606/9 |
| 5,312,400 | 5/1994 | Bales et al. | 606/41 |
| 5,314,406 | 5/1994 | Arias et al. | 604/21 |
| 5,320,618 | 6/1994 | Gustafsson | 606/9 |
| 5,322,507 | 6/1994 | Costello et al. | 128/4 |
| 5,324,254 | 6/1994 | Phillips | 604/21 |
| 5,326,343 | 7/1994 | Rudie et al. | 607/101 |
| 5,329,943 | 7/1994 | Johnson | 128/898 |
| 5,330,470 | 7/1994 | Hagen | 606/42 |
| 5,330,518 | 7/1994 | Neilson et al. | 607/101 |
| 5,334,140 | 8/1994 | Phillips | 604/35 |
| 5,334,183 | 8/1994 | Wuchinich | 606/46 |
| 5,336,217 | 8/1994 | Buys et al. | 606/9 |
| 5,336,220 | 8/1994 | Ryan et al. | 604/22 |
| 5,342,357 | 8/1994 | Nardella | 606/40 |
| 5,360,447 | 11/1994 | Koop | 623/15 |
| 5,366,443 | 11/1994 | Eggers et al. | 606/114 |
| 5,370,642 | 12/1994 | Keller | 606/9 |
| 5,370,675 | 12/1994 | Edwards et al. | 607/101 |
| 5,380,277 | 1/1995 | Phillips | 604/33 |
| 5,380,316 | 1/1995 | Aita et al. | 606/7 |
| 5,383,876 | 1/1995 | Nardella | 606/49 |
| 5,383,917 | 1/1995 | Desai et al. | 607/702 |
| 5,389,096 | 2/1995 | Aita et al. | 606/15 |
| 5,395,312 | 3/1995 | Desai | 604/22 |
| 5,403,311 * | 4/1995 | Abele et al. | 606/49 |
| 5,417,687 | 5/1995 | Nardella et al. | 606/32 |
| 5,419,767 | 5/1995 | Eggers et al. | 604/114 |
| 5,423,803 | 6/1995 | Tankovich | 606/9 |
| 5,425,728 | 6/1995 | Tankovich | 606/9 |
| 5,433,708 | 7/1995 | Nichols et al. | 604/113 |
| 5,441,499 | 8/1995 | Fritzsch | 606/45 |
| 5,445,634 | 8/1995 | Keller | 606/9 |
| 5,454,809 | 10/1995 | Janssen | 606/41 |
| 5,458,597 * | 10/1995 | Edwards et al. | 606/41 |
| 5,484,435 | 1/1996 | Fleenor et al. | 606/46 |
| 5,490,850 | 2/1996 | Ellman et al. | 606/45 |
| 5,507,790 | 4/1996 | Weiss | 607/100 |
| 5,514,130 | 5/1996 | Baker | 606/41 |
| 5,522,813 | 6/1996 | Trelles | 606/2 |
| 5,556,397 | 9/1996 | Long et al. | 606/48 |
| 5,569,242 | 10/1996 | Lax et al. | 606/42 |
| 5,578,029 | 11/1996 | Trelles et al. | 606/25 |
| 5,584,872 | 12/1996 | LaFontaine et al. | 607/116 |
| 5,609,151 | 3/1997 | Mulier et al. | 128/642 |
| 5,660,836 | 8/1997 | Knowlton | 424/400 |
| 5,676,693 | 10/1997 | LaFontaine et al. | 607/116 |
| 5,681,282 | 10/1997 | Eggers et al. | 604/114 |
| 5,683,366 | 11/1997 | Eggers et al. | 604/114 |
| 5,683,386 | 11/1997 | Ellman et al. | 606/41 |
| 5,683,387 | 11/1997 | Garito et al. | 606/45 |
| 5,695,495 | 12/1997 | Ellman et al. | 606/41 |
| 5,697,281 | 12/1997 | Eggers et al. | 604/114 |
| 5,697,536 | 12/1997 | Eggers et al. | 604/114 |
| 5,697,882 | 12/1997 | Eggers et al. | 604/114 |
| 5,697,909 | 12/1997 | Eggers et al. | 604/114 |
| 5,700,262 | 12/1997 | Acosta et al. | 606/48 |
| 5,725,524 | 3/1998 | Mulier et al. | 606/41 |
| 5,746,746 | 5/1998 | Garito et al. | 606/41 |
| 5,749,869 | 5/1998 | Lindenmeier et al. | 606/34 |
| 5,755,753 | 5/1998 | Knowlton | 607/98 |
| 5,766,153 | 6/1998 | Eggers et al. | 604/114 |
| 5,807,395 | 9/1998 | Mulier et al. | 606/41 |
| 5,810,764 | 9/1998 | Eggers et al. | 604/23 |
| 5,843,072 | 12/1998 | Furumoto et al. | 606/9 |

| | | |
|---|---|---|
| 5,843,078 | 12/1998 | Sharkey . |
| 5,868,744 * | 2/1999 | Willmen .................. 606/50 |
| 5,885,277 | 3/1999 | Korth ....................... 606/35 |
| 5,897,553 | 4/1999 | Mulier et al. ............ 606/41 |
| 5,913,864 | 6/1999 | Garito et al. ............. 606/131 |
| 5,931,807 | 8/1999 | McClure et al. ......... 604/27 |
| 5,944,715 | 8/1999 | Goble et al. ............. 606/41 |
| 5,947,964 * | 9/1999 | Eggers et al. ............ 606/41 |
| 5,948,011 | 9/1999 | Knowlton ................ 607/101 |
| 6,004,319 | 12/1999 | Goble et al. ............. 606/48 |
| 6,013,076 | 1/2000 | Goble et al. ............. 606/41 |
| 6,015,406 | 1/2000 | Goble et al. ............. 606/41 |
| 6,027,501 | 2/2000 | Goble et al. ............. 606/41 |
| 6,039,734 | 3/2000 | Goble et al. ............. 606/41 |
| 6,047,215 | 4/2000 | McClure et al. ......... 607/101 |
| 6,056,746 | 5/2000 | Goble et al. ............. 606/48 |

FOREIGN PATENT DOCUMENTS

| | | | |
|---|---|---|---|
| 0 597 463 | 5/1994 | (EP) | ............ A61N/5/04 |
| 0 703 461 A2 | 3/1996 | (EP) | ............ G01R/27/02 |
| 0 740 926 | 11/1996 | (EP) | ............ A61B/17/39 |
| 0 754 437 | 1/1997 | (EP) | ............ A61B/17/39 |
| 2308979 | 7/1997 | (GB) | ............ A61B/17/39 |
| 2308980 | 7/1997 | (GB) | ............ A61B/17/36 |
| 2308981 | 7/1997 | (GB) | ............ A61B/17/39 |
| 57-117843 | 7/1982 | (JP) | ............ A61B/17/39 |
| WO 90/07303 | 7/1990 | (WO) | ............ A61B/17/39 |
| WO 91/13650 | 9/1991 | (WO) | ............ A61N/5/04 |
| WO 92/21278 | 12/1992 | (WO) | ............ A61B/5/04 |
| WO 93/13816 | 7/1993 | (WO) | ............ A61B/17/36 |
| 93/20747 | 10/1993 | (WO) | ............ A61B/5/00 |
| WO 94/04220 | 3/1994 | (WO) | ............ A61N/1/06 |
| 94/08654 | 4/1994 | (WO) | ............ A61M/37/00 |
| WO 94/14383 | 7/1994 | (WO) | ............ A61B/17/36 |
| WO 94/26228 | 11/1994 | (WO) | ............ A61G/17/36 |
| 95/34259 | 12/1995 | (WO) | ............ A61F/5/48 |
| 96/00042 | 1/1996 | (WO) | ............ A61B/17/39 |
| 96/34568 | 11/1996 | (WO) . | |
| 97/00646 | 1/1997 | (WO) | ............ A61B/17/39 |
| 97/00647 | 1/1997 | (WO) | ............ A61B/17/39 |
| 97/15238 | 5/1997 | (WO) | ............ A61B/17/39 |
| 97/24073 | 7/1997 | (WO) | ............ A61B/17/39 |
| 97/24992 | 7/1997 | (WO) | ............ A61B/17/38 |
| 97/24993 | 7/1997 | (WO) | ............ A61B/17/39 |
| 97/24994 | 7/1997 | (WO) | ............ A61B/17/39 |
| 97/32532 | 9/1997 | (WO) | ............ A61B/17/39 |
| 97/48346 | 12/1997 | (WO) | ............ A61B/17/39 |
| 98/07468 | 2/1998 | (WO) . | |
| 98/11944 | 3/1998 | (WO) | ............ A61N/5/02 |
| 98/27879 | 7/1998 | (WO) | ............ A61B/17/36 |
| 98/38936 | 9/1998 | (WO) | ............ A61B/17/39 |

OTHER PUBLICATIONS

Rand et al. (1985) *J. Arthro. Surg.* 1:242–246 Effect of Electrocautery on Fresh Human Articular Cartilage.

V.E. Elsasser et al. *Acta Medicotechnica* vol. 24, No. 4, pp. 129–134 (1976).

E.V. Kramolowsky et al. *J. of Urology* vol. 143, pp. 275–277 (1990).

J.W. Ramsey et al. *Urological Research* vol. 13, pp. 99–102 (1985).

R. Tucker et al., Abstract P14–11, p. 248, "A Bipolar Electrosurgical Turp Loop".

R. Tucker et al. *J. of Urology* vol. 141, pp. 662–665, (1989).

R. Tucker et al. *Urological Research* vol. 18, pp. 291–294 (1990).

E. Kramolowsky et al. (1991) *J. of Urology* 146:669–674.

J. Pearce *Electrosurgery*, (1986) John Wiley & Sons, New York, pp. 17, 69–75 and 87.

Slager et al. (1985) *JACC* 5(6) : 1382–6.

Slager et al. (1987) *Z. Kardiol.* 76:Suppl. 6, 67–71.

* cited by examiner

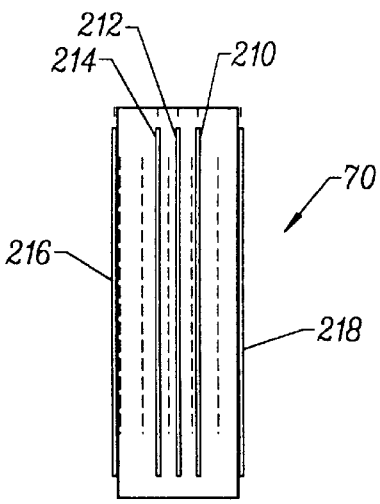
FIG. 6
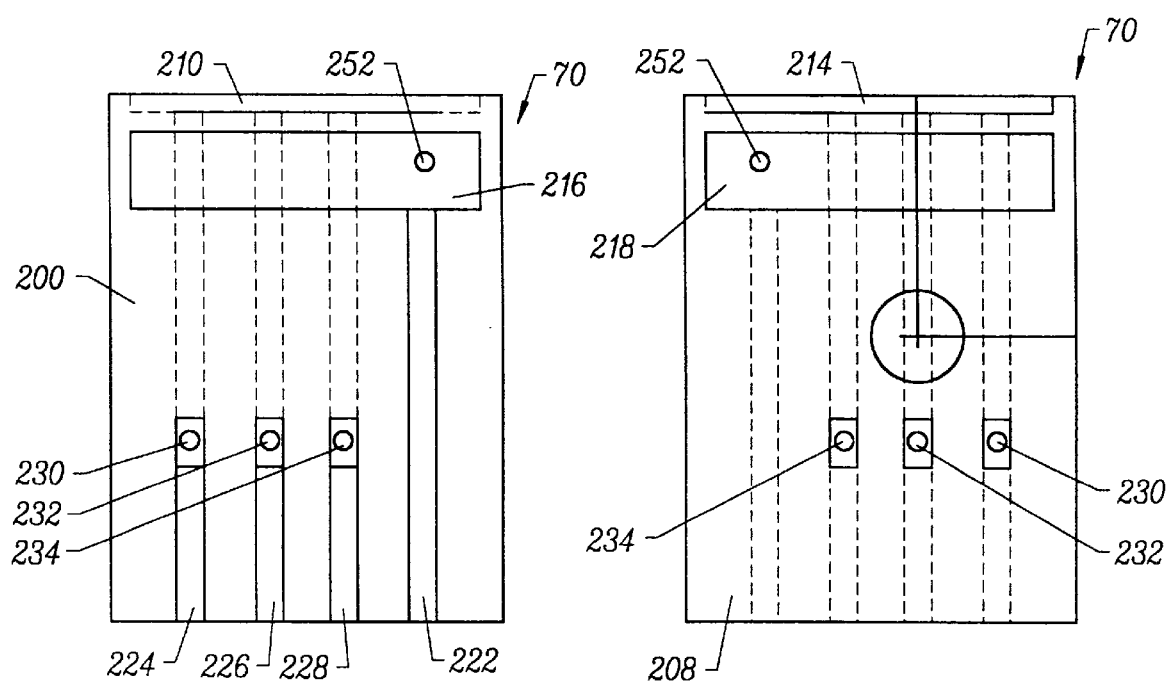
FIG. 7
FIG. 8

SYSTEMS AND METHODS FOR ELECTROSURGICAL TREATMENT OF VASCULAR DISORDERS

RELATED APPLICATIONS

The present invention is a continuation-in-part of U.S. patent application Ser. No. 08/977,845, filed Nov. 25, 1997, which is a continuation-in-part of application Ser. No. 08/562,332, filed Nov. 22, 1995, now U.S. Pat. No. 6,024,733, the complete disclosures of which are incorporated herein by reference for all purposes. The present invention also derives priority from U.S. patent application Ser. No. 09/130,804, filed Aug. 7, 1998, now U.S. Pat. No. 6,045,532, the complete disclosure of which is incorporated herein by reference.

The present invention is related to commonly assigned co-pending U.S. patent application Ser. Nos. 09/162,110 and 09/162,117, filed Sep. 28, 1998, and U.S. Pat. No. 08/990,374, filed Dec. 15, 1997, which is a continuation-in-part of U.S. patent application Ser. No. 08/485,219, filed on Jun. 7, 1995, now U.S. Pat. No. 5,697,281, U.S. patent application Ser. Nos. 09/109,219, 09/058,571, 08/874,173 and 09/002,315, filed on Jun. 30, 1998, Apr. 10, 1998, Jun. 13, 1997, and Jan. 2, 1998, respectively and U.S. patent application Ser. No. 09/054,323, filed on Apr. 2, 1998, U.S. patent application Ser. No. 09/010,382, filed Jan. 21, 1998, and U.S. patent application Ser. No. 09/032,375, filed Feb. 27, 1998, U.S. patent application Ser. Nos. 08/977,845, filed on Nov. 25, 1997, 08/942,580, filed on Oct. 2, 1997, U.S. patent application Ser. No. 08/753,227, filed on Nov. 22, 1996, U.S. patent application Ser. No. 08/687,792, filed on Jul. 18, 1996, and PCT International Application, U.S. National Phase Serial No. PCT/US94/05168, filed on May 10, 1994, now U.S. Pat. No. 5,697,909, which was a continuation-in-part of U.S. patent application Ser. No. 08/059,681, filed on May 10, 1993, which was a continuation-in-part of U.S. patent application Ser. No. 07/958,977, filed on Oct. 9, 1992 which was a continuation-in-part of U.S. patent application Ser. No. 07/817,575, filed on Jan. 7, 1992, the complete disclosures of which are incorporated herein by reference for all purposes. The present invention is also related to commonly assigned U.S. Pat. No. 5,683,366, filed Nov. 22, 1995 the complete disclosure of which is incorporated herein by reference for all purposes.

BACKGROUND OF THE INVENTION

The present invention relates generally to the field of electrosurgery, and more particularly to surgical devices and methods which employ high frequency electrical energy to treat vascular disorders, such as, cutaneous vascular lesions, port wine stains, face veins, telangiectasis, spider veins, birth marks and the like.

A cutaneous vascular lesion, such as telangiectasis or spider capillaries of the lower extremities, is a condition where previously microscopic blood vessels have become dilated. They are visible through the skin appearing as red, blue or purple variably tortuous lines or patches. The causes of this abnormal enlargement of vessels are not fully understood, and although they are of little medical consequence, their cosmetic significance can be great.

The most common treatment used for cutaneous vascular lesions is sclerotherapy, which entails the intravascular injection of one of a variety of agents into the abnormal blood vessels. The injected substance injures the interior walls of the capillary causing it to shrink or disappear. Unfortunately, this treatment can be painful, only partially effective, and usually requires about one to two months waiting before improvement can be seen. In addition, undesirable side effects can occur, such as echymotic or hyperpigmented marks, which may take months to completely fade away.

In the treatment of vascular lesions, a variety of different lasers (e.g., CO2, Argon, tunable dye, pulsed dye, KTP, Nd/Yag) have been used to irradiate the surface of the skin. The laser energy penetrates through the skin and is absorbed by the constituents in the blood, which coagulates and collapses the vein. Unfortunately, there are also problems associated with the use of lasers in these procedures. For example, although most of the laser energy passes through the tissue to the vessel, scattering and absorption of the light take place in the tissue. This absorption can cause significant changes in skin coloration and even scarring. In addition, if the laser energy is delivered over too long a period, significant thermal damage will occur in regions beyond the vein being treated. Moreover, the interaction between laser light and melanin pigments in the epidermis that overlies the target vessels can cause long term hyperpigmentation, persistent scabs and sometimes permanent scarring.

SUMMARY OF THE INVENTION

The present invention provides systems, apparatus and methods for selectively applying electrical energy to blood vessels within the body, and is particularly useful for treating vascular disorders.

In one aspect of the invention, a method for treating a discolored blood vessel in tissue under the surface of the skin is provided. In this method, one or more active electrode(s) are positioned in close proximity to a target region of the blood vessel, and a sufficient high frequency voltage is applied to the electrode terminal(s) to cause thermal damage to a target region within the blood vessel. The thermal injury causes the vessel to shrink, or to thrombose and collapse, so that blood flow through the vessel is restricted or completely interrupted. Preferably, the vessel is injured with minimal thermal energy being applied to the surrounding tissue, which prevents the tissue discoloration or scarring associated with prior art thermal processes. The electrode terminal(s) may be positioned on the external surface of the skin, or they may be introduced through a percutaneous penetration in the outer skin surface to the blood vessel. In the latter embodiment, the percutaneous penetration may be formed by advancing one or more needle electrodes through the outer surface of the skin to the target region of the vessel. Alternatively, this percutaneous penetration may be generated by applying sufficient electrical energy to the electrode terminal(s) to remove or ablate a portion of the outer skin surface. In this latter embodiment, the electrode terminal(s) are advanced axially through the skin to volumetrically remove or ablate a hole or channel from the skin surface to the blood vessel. A more complete description of systems and methods for boring channels through tissue with RF energy can be found in commonly assigned U.S. Pat. No. 5,683,366, the complete disclosure of which is incorporated herein by reference.

In a specific embodiment, a needle electrode is inserted through the patient's skin such that a distal portion of the needle electrode is located in close proximity to the target region of the blood vessel. High frequency voltage is then applied between the needle electrode and a return electrode to effect coagulation and/or necrosis of the blood vessel. In the representative embodiment, the needle electrode is an insulated acupuncturesized needle having a diameter in the range of about 0.05 to about 2.0 mm, preferably less than 1 mm in diameter. A selected length of the distal portion of the needle is exposed (e.g., typically less than about 3 mm and preferably less than abut 0.5 mm) to allow current to flow from needle to the surrounding tissue and blood vessel. The needle is inserted through the patient's skin to the target region of the blood vessel, and high frequency voltage is applied such that a current flows from the exposed portion of the needle through the target region and to the return electrode.

In this aspect of the invention, the return electrode may be positioned on the surface of the patient's skin, or it may be introduced through the skin to a location in close proximity to the target region of the blood vessel. In the latter embodiment, the return electrode may be located on the insulated needle (e.g., as a second exposed portion spaced and electrically isolated from the active exposed portion), or it may be part of a separate instrument. In the representative embodiment, the return electrode comprises a thin, insulated, conductive needle having an inner lumen for receiving the active needle electrode, and an exposed distal portion for completing the current return path from the active needle electrode. The active needle electrode is preferably axially movable relative to the return electrode such that the distance between the two exposed portions of the electrodes can be varied during the procedure. This allows the surgeon to control the zone of necrosis around the target region. The bipolar modality of the present invention confines the electric currents to the target region, minimizing thermal injury to surrounding skin tissue.

In the representative embodiment, the return electrode needle includes a fluid lumen for delivering fluid to the target site. Preferably, the return electrode is a hollow needle having a central lumen for fluid delivery and for receiving the active electrode needle. In one embodiment, electrically conductive fluid, such as isotonic saline, is delivered to the target site to decrease the tissue resistance around the target site. This will increase the effectiveness of the device by reducing tissue heating around the target site, and by further confining the electric current to the target, thereby reducing collateral tissue damage. In another embodiment, a local anesthetic is delivered alone, or in combination with a conductive fluid, to the target region such that the procedure may be performed in the doctor's office under local anesthesia. The present invention may be used in combination with a tumescent technique for delivering a relatively large volume of a dilute solution of a local anesthetic agent and/or a vasoconstrictor agent to the target site. The anesthetic and vasoconstrictor agents may be dilute in a solution of, for example, electrically conductive fluid.

The system may optionally include a temperature controller coupled to one or more temperature sensors at or near the distal end of the active or return electrode(s). The controller adjusts the output voltage of the power supply in response to a temperature set point and the measured temperature value. The temperature sensor may be, for example, a thermocouple, located on the return electrode that measures a temperature at the distal end of the return electrode. In this embodiment, the temperature set point will preferably be one that corresponds to a tissue temperature that results in the coagulation of blood, i.e., about 60° C. to 70° C., without exceeding this range. This helps to limit thermal injury to surrounding tissue.

In one embodiment, the system of the present invention will include a depth measuring device for determining the depth of penetration of the active and return electrodes from the outer surface of the patient's skin. This allows precise placement of the electrodes at the target region, and allows the surgeon to more precisely determine the distance between the active and return electrodes. In the representative embodiment, the depth measuring device includes a plurality of depth indicia on one or both of the active and return electrodes for determining the relative depths of the electrodes.

In another aspect of the invention, a method is provided for intravascular occlusion of body lumens, particularly for treating intracranial aneurysms. In this method, a sufficient amount of electrical energy is applied to the body lumen to cauterize or coagulate the blood within the vessel to occlude the vessel without causing excessive tissue damage. In one method, a catheter is delivered, typically intravascularly, to a location within or near the neck of the aneurysm or other vascular opening to be occluded. High frequency voltage is applied to one or more active electrode(s) on the catheter to heat and coagulate the surrounding blood and tissue to effectively occlude the body lumen. In the preferred embodiment, the catheter includes a return electrode spaced from the active electrode(s) to confine the electric current to, and around, the target site. Electrically conductive fluid may optionally be delivered to the target site to facilitate current conduction between the electrodes. In addition, the catheter may include a temperature sensor to either track, or to control (e.g., with feedback), the temperature at the target site.

A further understanding of the nature and advantages of the invention will become apparent by reference to the remaining portions of the specification and drawings.

BRIEF DESCRIPTION OF THE DRAWINGS

FIG. 6 is an end view of an exemplary electrode support comprising a multi-layer wafer with plated conductors for electrodes;

FIGS. 7 and 8 are side views of the electrode support of FIG. 7;

FIGS. 9A–13A are side views of the individual wafer layers of the electrode support;

FIGS. 9B–13B are cross-sectional views of the individual wafer layers;

DESCRIPTION OF SPECIFIC EMBODIMENTS

Figure 1:
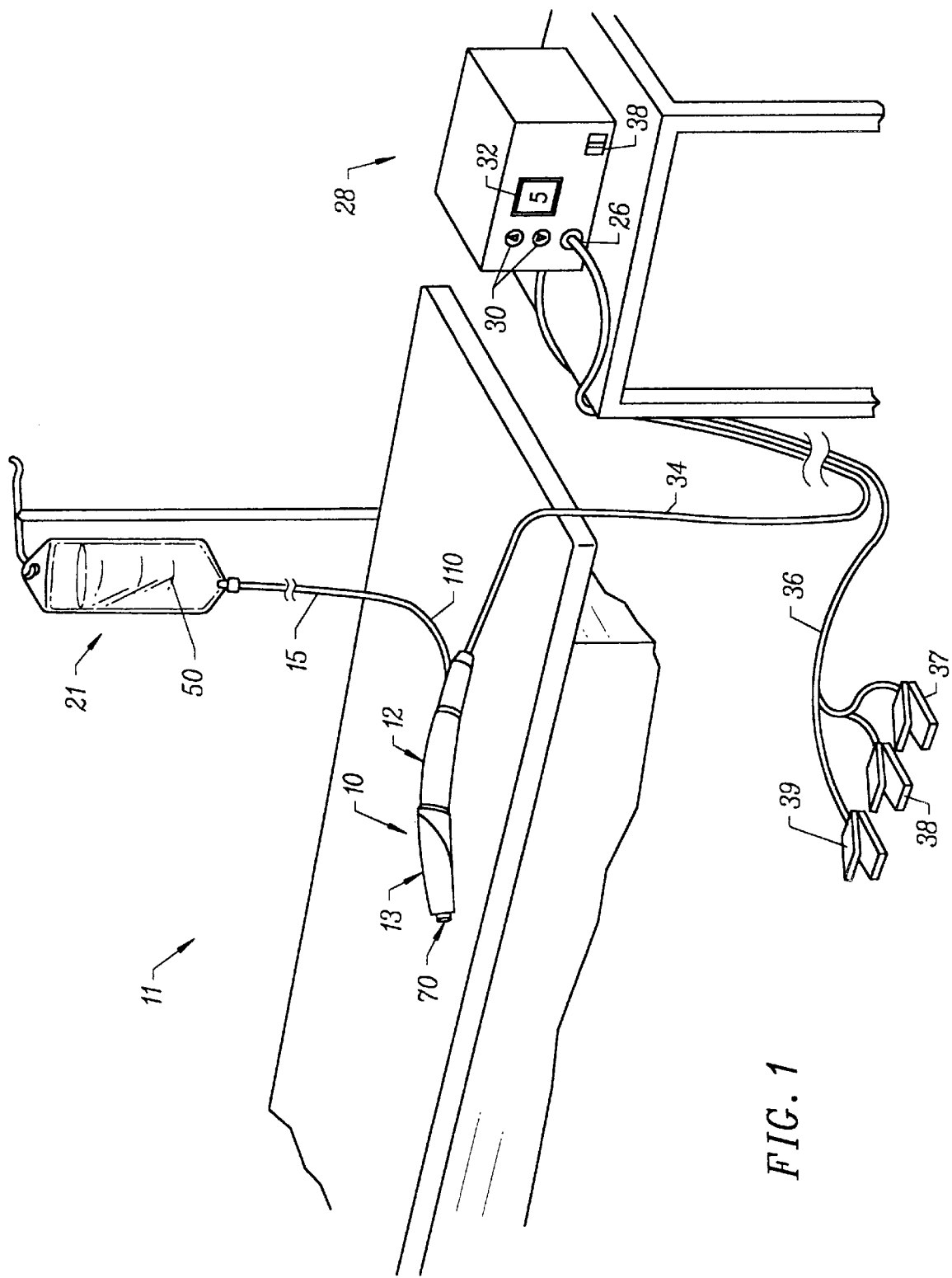
FIG. 1 is a perspective view of an electrosurgical system for treating a patient's skin including an electrosurgical generator and an electrosurgical probe or handpiece.

The present invention provides systems and methods for selectively applying electrical energy to a target location within or on a patient's body, particularly including procedures on or near an external body surface, such as epidermal and dermal tissues in the skin, or the underlying cutaneous tissue. For convenience, the remaining disclosure will be directed specifically to procedures for treating vascular disorders, such as port wine stains, face veins, telangiectasis, birth marks, and the like. However, it will be appreciated that the present invention may also be useful for skin tissue cutting, ablation, incising or removal in the epidermis or dermis, e.g., the removal of pigmentations, scars, tattoos, etc., and for other surgical procedures on the skin, such as tissue rejuvenation, blepharoplasty, browlifts, cosmetic surgery, wrinkle removal, hair removal and/or transplant procedures. In addition, the systems and methods can be applied equally well to procedures involving other tissues of the body, as well as to other procedures including open surgery, arthroscopic surgery, laparoscopic surgery, thoracoscopic surgery, and other endoscopic surgical procedures.

The present invention applies high frequency (RF) electrical energy to one or more electrode terminals to cause thermal injury of the interior of blood vessels underlying the surface of the skin. The thermal injury causes the blood vessel to shrink or to thrombose and collapse, which prevents blood from flowing through the vessel. In some embodiments, the present invention is used for treating a discolored blood vessel under the surface of the skin, as described above.

In other embodiments, the present invention may be used to occlude vessels by causing sufficient thermal injury within the vessel to coagulate the blood therein. In this embodiment, the present invention may be used to treat aneurysms, vascular malformations, arteriovenous fistulas (e.g., carotid-cavernous, vertebral), internal arterial bleeding sites, arteries feeding vascular tumors, damaged vessels following trauma and the like. The techniques of the present invention may be performed percutaneously by introducing an electrosurgical instrument into the patient's vasculature and advancing the instrument transluminally to a target site. These procedures may also be performed through other minimally invasive methods, such as introducing a surgical probe and endoscope through a small opening, e.g., a burr hole, in the patient's cranium, or through natural openings in the patient's head, such as transoral or transsphenoidal procedures. The present invention may further be performed using traditional open surgery techniques.

In procedures in or around the brain, the techniques of the present invention will typically be performed in conjunction with instrument guiding technology for guiding the surgical instrument to the target site within the head and neck, e.g., the brain. In this regard, the present invention may use a variety of imaging techniques, such as computerized tomography (CT) scanning, magnetic resonance imaging (MRI), ultrasound, angiography, radionucleotide imaging, electroencephalography (EEG) and the like. In conjunction with one of these imaging procedures, typically CT or MRI, the present invention may also use compatible stereotactic systems for guiding the instrument to the target location. In standard stereotactic systems, a frame, e.g., a Leksell, Todd-Wells or Guiot frame, fixes the patient's head to the image. These frames, combined with radiological landmarks and a brain atlas, provide anatomical localization to within +−1 mm. Alternatively, imaged guided frameless stereotactic systems that utilize modern imaging, elaborate computer software and a locating device, may be employed with the present invention.

The electrosurgical instrument will comprise a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. For dermatology procedures, the shaft will have any suitable length and diameter that would facilitate handling by the surgeon. For treating vessels underneath the surface of the skin, the active electrode shaft will preferably have a small diameter to minimize trauma, e.g., on the order of about 0.05 mm to about 2.0 mm, preferably less than about 1.0 mm. Similarly, the return electrode shaft with either be the same shaft as the active electrode shaft, or a separate shaft having a diameter on the order of a about 0.05 to 5 mm, preferably less than about 2.0 mm. For intravascular procedures, the shaft will comprise a conventional or specialized guide catheter, or the invention may include a catheter having an active electrode or electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The catheter haft will usually include a plurality of wires or other conductive elements running axially therethrough to permit connection of the electrode or electrode array and the return electrode to a connector at the proximal end of the catheter shaft. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific shaft designs will be described in detail in connection with the figures hereinafter.

In some embodiments, the active electrode(s) may be supported within or by an inorganic insulating support positioned near the distal end of the instrument shaft. In other embodiments that do not involve the generation of a plasma layer for removal of tissue (e.g., treating vascular disorders), the active electrode(s) may be supported by other materials, e.g., plastic, or the entire shaft may be electrically conductive, having an outer insulating jacket to minimize current flow to collateral tissue. The return electrode may be located on the instrument shaft, on another instrument or on the external surface of the patient (i.e., a dispersive pad). The close proximity of nerves and other sensitive tissue in the face, however, makes a bipolar design more preferable because this minimizes the current flow through healthy tissue and surrounding nerves. Accordingly, the return electrode is preferably either integrated with the instrument body, or another instrument located in close proximity to the distal end of the instrument. The proximal end of the instrument will include the appropriate electrical connections for coupling the return electrode(s) and the electrode terminal(s) to a high frequency power supply, such as an electrosurgical generator.

In some embodiments, the current flow path between the electrode terminals and the return electrode(s) may be improved by submerging the tissue site in an electrical conducting fluid (e.g., within a viscous fluid, such as an electrically conductive gel) or by directing an electrically conducting fluid along a fluid path to the target site (i.e., a liquid, such as isotonic saline, or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conducting fluid between the active and return electrodes is described in U.S. Pat. No. 5,697,281, previously incorporated herein by reference. Alternatively, the body's natural conductive fluids, such as blood, may be sufficient to establish a conductive path between the return electrode(s) and the electrode terminal(s), and to provide the conditions for establishing a vapor layer, as described above. However, in some embodiments designed to ablate tissue conductive fluid that is introduced to the patient is generally preferred over blood because blood will tend to coagulate at certain temperatures. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply may include a fluid interlock for interrupting power to the electrode terminal(s) when there is insufficient conductive fluid around the electrode terminal (s). This ensures that the instrument will not be activated when conductive fluid is not present, minimizing the tissue damage that may otherwise occur. A more complete description of such a fluid interlock can be found in commonly assigned, co-pending U.S. patent application Ser. No. 09/058,336, filed Apr. 10, 1998, the complete disclosure of which is incorporated herein by reference.

In some procedures, it may also be necessary to retrieve or aspirate the electrically conductive fluid and/or the gaseous or liquid products of the procedure. For example, in procedures in and around the brain and its surrounding blood vessels, it may be desirable to aspirate the fluid so that it does not flow downstream. In addition, it may be desirable to aspirate small pieces of tissue or other body structures that are not completely disintegrated by the high frequency energy, or other fluids at the target site, such as blood, mucus, the gaseous products of ablation, etc. Accordingly, the system of the present invention may include one or more suction lumen(s) in the instrument, or on another instrument, coupled to a suitable vacuum source for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation electrode terminal(s), or the same electrode(s) may serve both functions. A more complete description of instruments incorporating aspiration electrode(s) can be found in commonly assigned, co-pending patent application Ser. No. 09/010, 382, filed Jan. 21, 1998, the complete disclosure of which is incorporated herein by reference.

As an alternative or in addition to suction, it may be desirable to contain the excess electrically conductive fluid, tissue fragments and/or gaseous products of ablation at or near the target site with a containment apparatus, such as a basket, retractable sheath or the like. This embodiment has the advantage of ensuring that the conductive fluid, tissue fragments or ablation products do not flow through the patient's vasculature or into other portions of the body. In addition, it may be desirable to limit the amount of suction to limit the undesirable effect suction may have on hemostasis of severed blood vessels.

The present invention may use a single active electrode terminal or an electrode array distributed over a contact surface of an instrument. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive liquids, such as blood, normal saline, electrically conductive gel and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the probe to form a single wire that couples to a power source.

In one configuration, each individual electrode terminal in the electrode array is electrically insulated from all other electrode terminals in the array within said probe and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the probe may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode may be a tubular member of conductive material proximal to the electrode array at the tip which also serves as a conduit for the supply of the electrically conducting fluid between the active and return electrodes. The application of high frequency voltage between the return electrode and the electrode array results in the generation of high electric field intensities at the distal tips of the electrode terminals with conduction of high frequency current from each individual electrode terminal to the return electrode. The current flow from each individual electrode terminal to the return electrode is controlled by either active or passive means, or a combination thereof, to deliver electrical energy to the surrounding conductive fluid while minimizing energy delivery to surrounding (non-target) tissue.

The application of a high frequency voltage between the return electrode and the electrode array for appropriate time intervals effects heating of the conductive fluid and contraction of the target tissue. The tissue volume over which energy is dissipated (i.e., a high current density exists) may be precisely controlled, for example, by the use of a multiplicity of small electrode terminals whose effective diameters or principal dimensions range from about 10 mm to 0.01 mm, preferably from about 5 mm to 0.05 mm, and more preferably from about 3 mm to 0.1 mm. Electrode areas for both circular and non-circular terminals will have a contact area (per electrode terminal) below 25 $mm^2$, preferably being in the range from 0.0001 $m^2$ to 1 $mm^2$, and more preferably from 0.005 $mm^2$ to 0.5 $mm^2$. The circumscribed area of the electrode array is in the range from 0.25 $mm^2$ to 75 $mm^2$, preferably from 0.5 $mm^2$ to 40 $mm^2$, and will usually include at least two isolated electrode terminals and preferably about three electrode terminals. Of course, the array may include more than three electrode terminals (e.g., 50 or more electrode terminals) disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

In the above procedures, the electrode terminal(s) are formed over a tissue treatment surface on the shaft of the electrosurgical probe. The return electrode surface will be recessed relative to the distal end of the probe and may be recessed within a fluid conduit provided for the introduction of electrically conducting fluid to the site of the target tissue and electrode terminal(s). The area of the tissue treatment surface can vary widely, and the tissue treatment surface can assume a variety of geometries, with particular areas and geometries being selected for specific applications. Active electrode surfaces can have areas in the range from 0.25 $mm^2$ to 75 $mm^2$, usually being from about 0.5 $mm^2$ to 40 $mm^2$. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic procedures.

In one embodiment, the electrode array comprises a plurality of substantially elongate electrode terminals spaced on the contact surface of the shaft. Preferably, the contact surface is an electrically insulating electrode support member extending from the shaft of the probe. The elongate electrode terminals will typically have a length of about 0.5 to 30 mm, preferably about 1 to 15 mm and more preferably about 3 to 7 mm. The width of the elongate electrode terminals is usually about 0.01 to 2 mm, preferably about 0.05 to 1 mm, and more preferably about 0.1 to 0.5 mm. The elongate electrode terminals will be spaced from each other by a distance of about 0.05 to 4 mm, preferably about 0.1 mm to 2 mm. Although the array may comprise one electrode terminal or over 50 electrode terminals, applicant has found that two to ten electrode terminals provides a substantially uniform application of energy to the tissue at the treatment site.

For treating the surface of a patient's skin (e.g., skin resurfacing procedures), the electrode support comprises a plurality of wafer layers bonded together, e.g., by a glass adhesive or the like. The wafer layers each have conductive strips printed thereon to form the electrode terminal(s) and the return electrode(s). In one embodiment, the proximal end of the wafer layers will have a number of holes extending from the conductor strips to an exposed surface of the wafer layers for connection to electrical conductor lead traces in the electrosurgical probe or handpiece. The wafer layers preferably comprise a ceramic material, such as alumina, and the electrode will preferably comprise a metallic material, such as gold, platinum, palladium, tungsten, silver or the like. Suitable multilayer ceramic electrodes are commercially available from e.g., VisPro Corporation of Beaverton, Oreg.

In those embodiments in which an electrically conductive fluid is desired, the fluid should have a threshold conductivity to provide a suitable conductive path between the return electrode and the electrode terminal(s). The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm. Alternatively, the fluid may be an electrically conductive gel or spray, such as a saline electrolyte gel, a conductive ECG spray, an electrode conductivity gel, an ultrasound transmission or scanning gel, or the like. Suitable gels or sprays are commercially available from Graham-Field, Inc. of Hauppauge, N.Y. In addition, other electrically conductive fluids may be used, as described in Provisional Application Ser. No. 60/098,122, filed Aug. 27, 1998, the complete disclosure of which is incorporated herein by reference.

In some embodiments, the electrode support and the fluid outlet may be recessed from an outer surface of the probe or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor or plasma layer between the electrode terminal(s) and the tissue at the treatment site throughout the procedure, which reduces the thermal damage that might otherwise occur if the vapor layer were extinguished due to a lack of conductive fluid. The electrically conductive fluid also helps maintain the tissue temperature as low as possible during the procedure.

The voltage applied between the return electrode and the electrode array will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the electrode terminal size, the operating frequency and the operation mode of the particular procedure or desired effect on the tissue (i.e., contraction, coagulation or ablation). Typically, the peak-to-peak voltage will be in the range of 10 to 2000 volts and preferably in the range of 20 to 1200 volts and more preferably in the range of about 40 to 800 volts (again, depending on the electrode size, the operating frequency and the operation mode).

Figure 21:
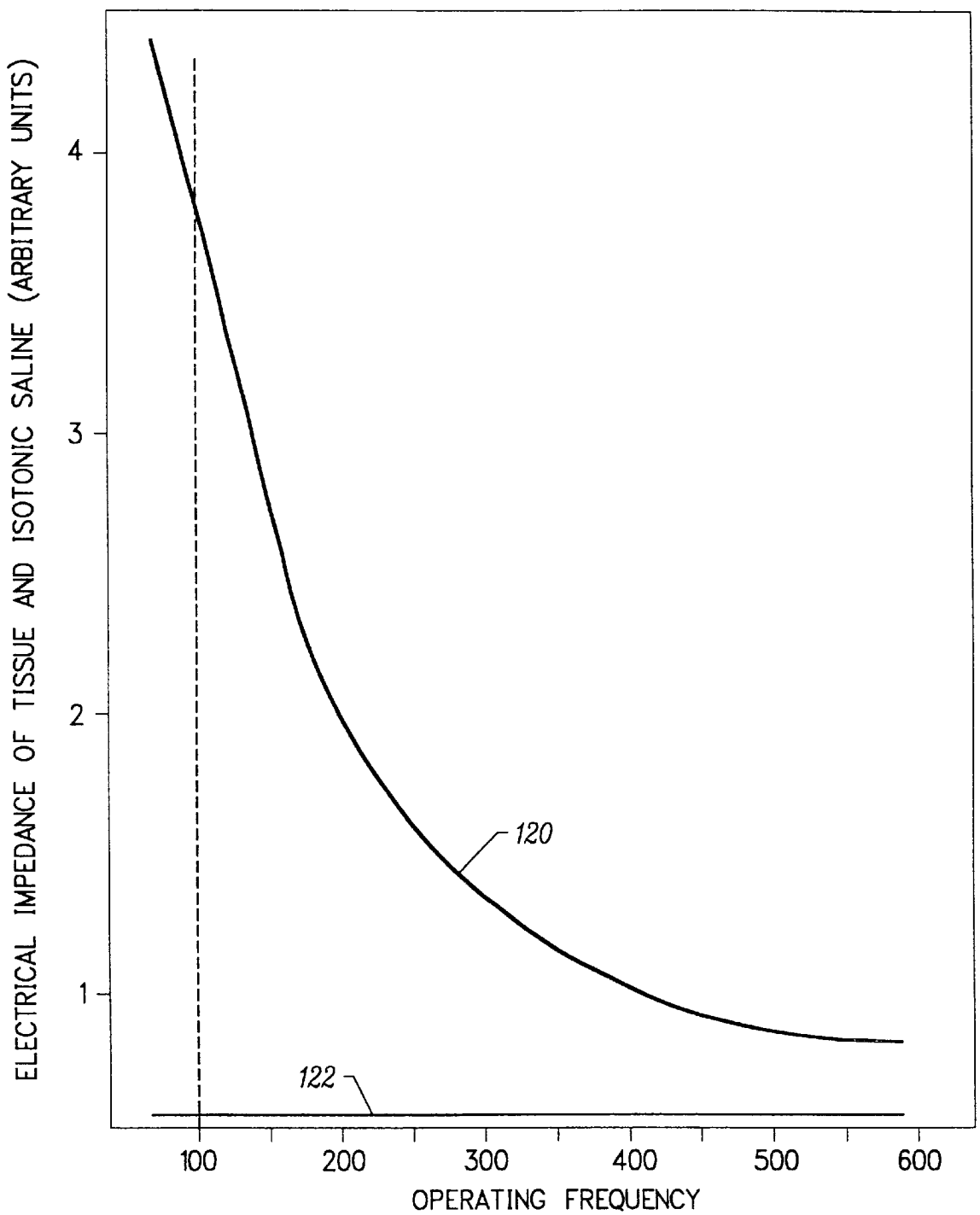
FIG. 21 is a graph illustrating the electrical impedance of tissue and isotonic saline with operating frequency.

An important aspect of certain aspects of the present invention is the discovery that the frequency of the output voltage of the generator can be selected to control the depth of tissue heating. Referring to FIG. 21, the electrical impedance of tissue is known to decrease with increasing frequency due to the electrical properties of cell membranes which surround electrically conductive cellular fluid. As shown, the electrical impedance of tissue to current at a frequency of 100 kHz is on the order of four times larger than at a frequency of 450 to 500 kHz. As a result of the higher tissue impedance, the current flux lines tend to penetrate less deeply resulting in a smaller depth of tissue heating. This principle of operation of the present invention can be used to advantage in applications where the depth of tissue heating is to be maintained small (e.g., 0.2 to 0.5 mm). Preferably, the operating frequency should be below 350 kHz for applications requiring shallow depths of tissue heating (e.g., less than 10.5 mm). Conversely, in situations where much larger depths of tissue heating are to be effected, a higher output voltage frequency may be used. By way of example, to achieve therapeutic collagen shrinkage to a depth of 1.5 to 3.0 mm, a higher operating frequency may be used (e.g., 500 kHz). Alternatively, the diameter of the electrode terminals and/or the spacing between the outer perimeter of the electrode terminals and the electrode support member may be selected to increase the depth of current penetration. By way of example, increasing the distance between the outer perimeter of the support member and the electrode terminals will increase the depth of heating for a given operating frequency.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, the total number of electrode(s) and/or the maximum allowed temperature selected for the probe tip. The power source allows the user to select the voltage level according to the specific requirements of a particular arthroscopic surgery, cosmetic surgery, dermatological procedure, ophthalmic procedures, open surgery or other endoscopic surgery procedure. A description of a suitable power source can be found in U.S. Provisional Patent Application No. 60/062,997, filed on Oct. 23, 1997, the complete disclosure of which has been previously incorporated herein by reference.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the size of the electrode terminal(s), the desired tissue heating rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel).

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source.

FIGS. 1–17 illustrate systems and methods designed for treating a patient's skin, such as scar removal or skin resurfacing procedures. Referring to FIG. 1, an electrosurgical system 11 generally comprises an electrosurgical handpiece or probe 10 connected to a power supply 28 for providing high frequency voltage to a target site and a fluid source 21 for supplying electrically conducting fluid 50 to probe 10. Probe 10 generally includes a proximal handle 12 and a distal tip 13 having an electrode support member 70 with one or an array of electrode terminals 58 and one or more return electrodes 100, 102 (see FIGS. 2, 4 and 5) disposed on the support member 70. A connecting cable 34 has a connector 26 for electrically coupling the electrodes in probe 10 to power supply 28. The electrode terminals 58 are electrically isolated from each other and each of the terminals 58 is connected to an active or passive control network within power supply 28 by means of a plurality of individually insulated conductors (not shown). A fluid supply tube 15 is connected to a fluid tube 110 of probe 10 for supplying electrically conducting fluid 50 to the distal tip 13 (see FIGS. 16 and 17).

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjusting the energy level applied to electrode terminals 58. In an exemplary embodiment, first foot pedal 37 is used to place the power supply into the "ablation" mode and second foot pedal 38 places power supply 28 into the "coagulation" mode. The third foot pedal 39 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing the vapor layer and accelerating these charged particles against the tissue). As discussed above, the requisite voltage level for ablation will vary depending on the number, size, shape and spacing of the electrodes, the distance in which the electrodes extend from the support member, etc. When the surgeon is using the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the coagulation mode, the power supply 28 applies a low enough voltage to one or more electrode terminals (or one or more coagulation electrodes) to avoid vaporization of the electrically conductive fluid, formation of a plasma and subsequent molecular dissociation of the tissue. The surgeon may automatically toggle the power supply between the ablation and coagulation modes by alternatively stepping on foot pedals 37, 38, respectively. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulate small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37. A specific design of a suitable power supply for use with the present invention can be found in U.S. Provisional Patent Application 60/062,997, filed Oct. 23, 1997.

Figure 2:
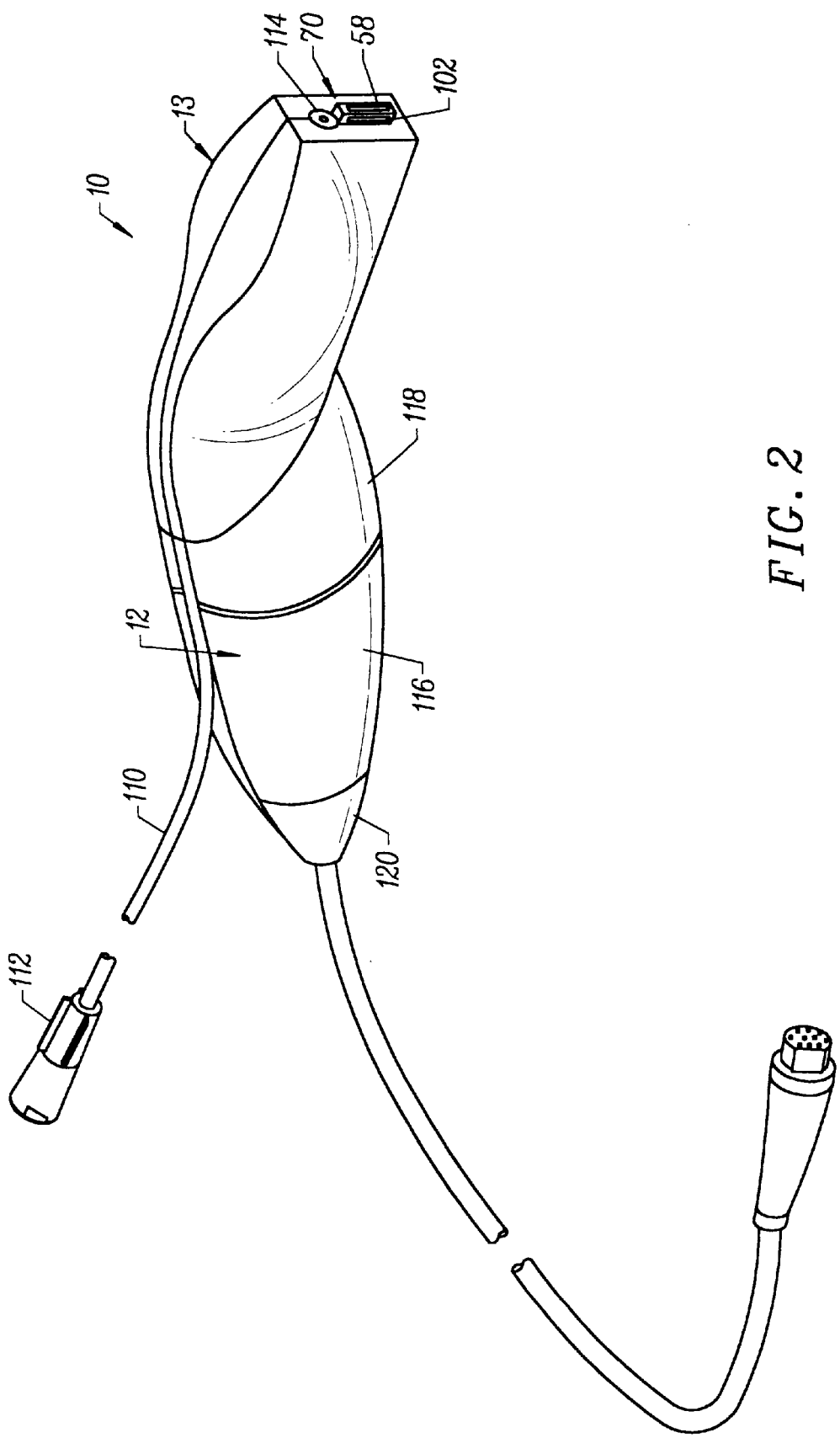
FIG. 2 is a perspective view of one embodiment of an electrosurgical probe constructed according to the principles of the present invention.
Figure 3A:
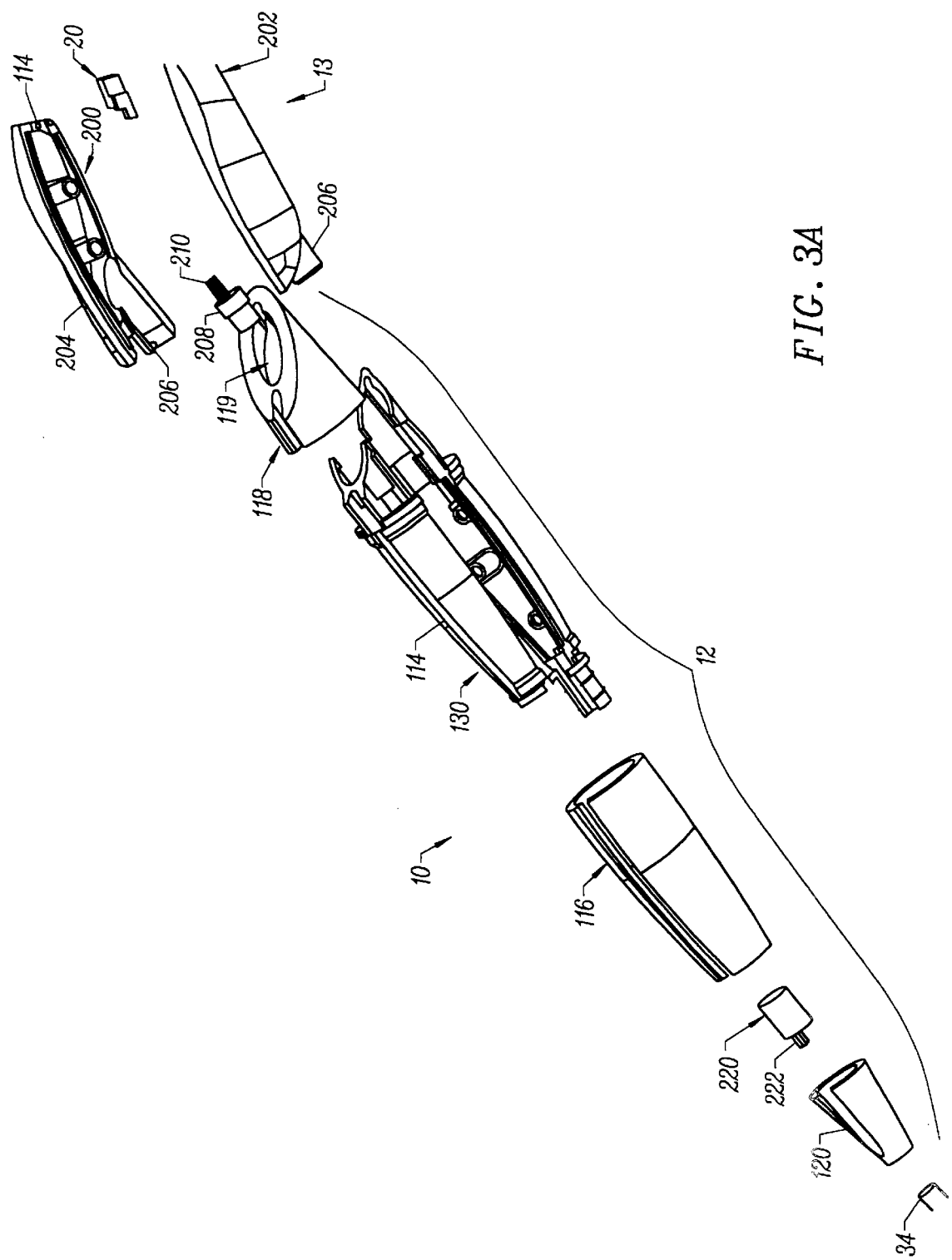
FIGS. 3A–3C are exploded, isometric views of the probe of FIG. 2.
Figure 3B:
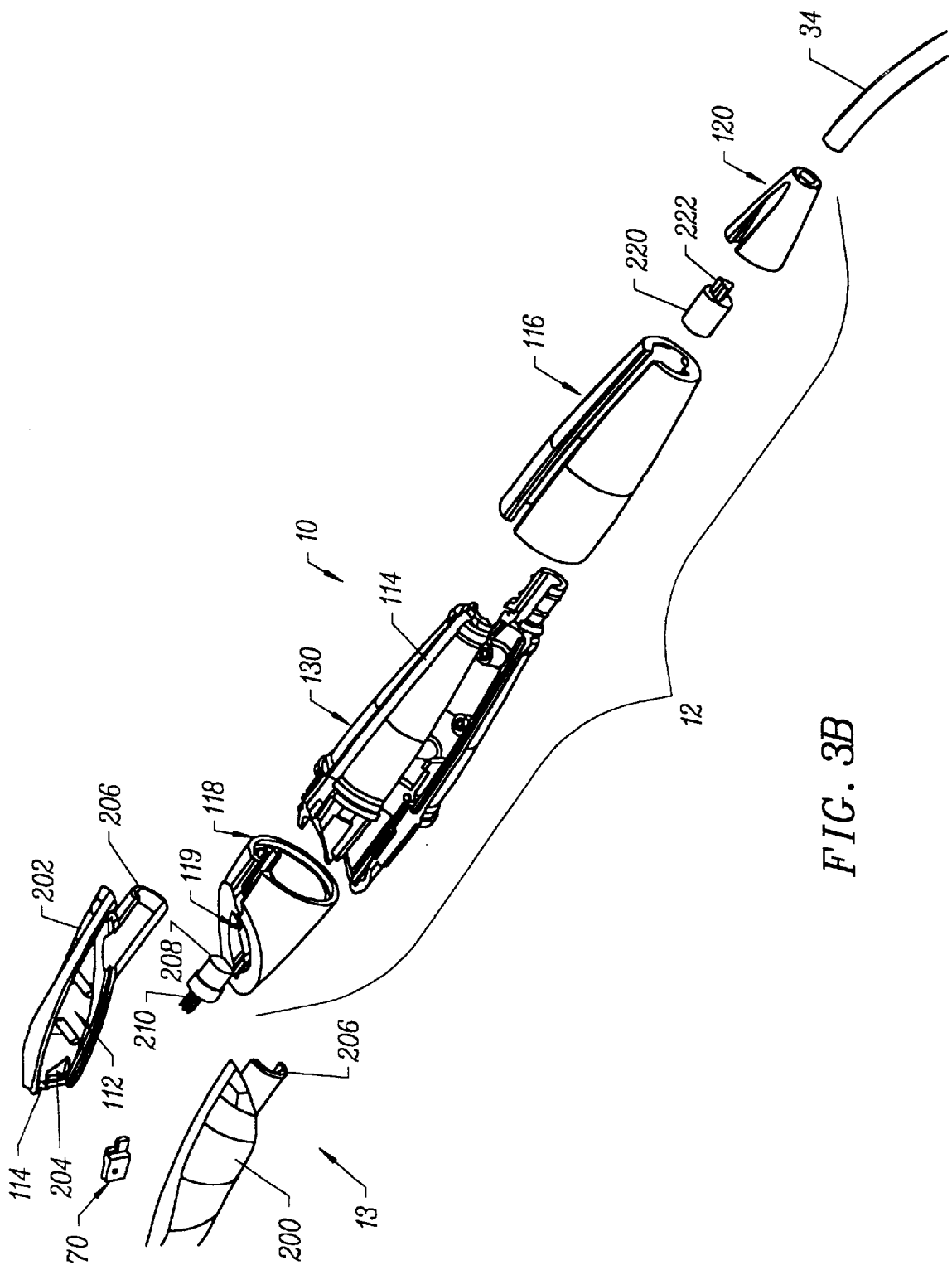
Figure 3C:
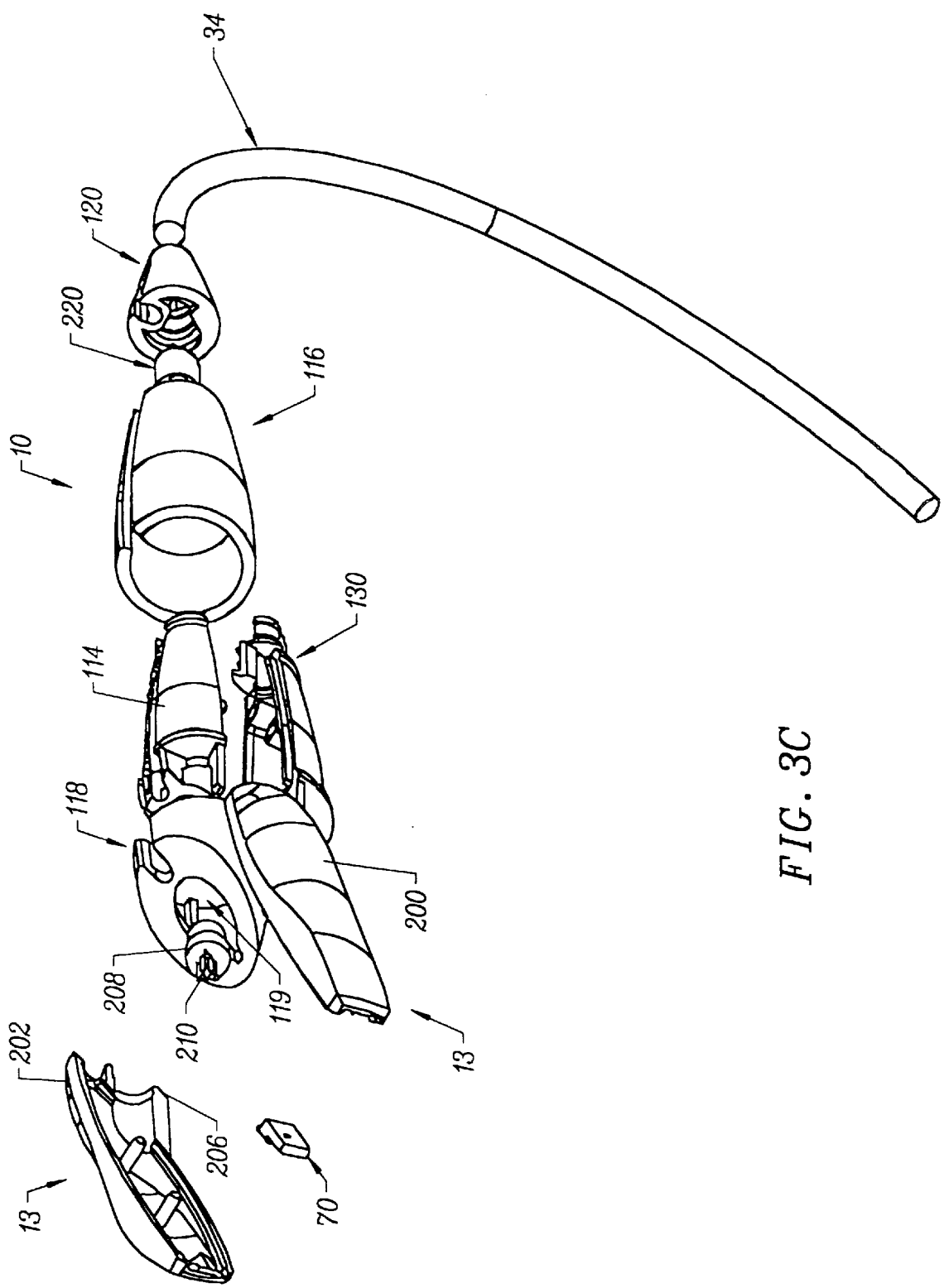
Figure 5:
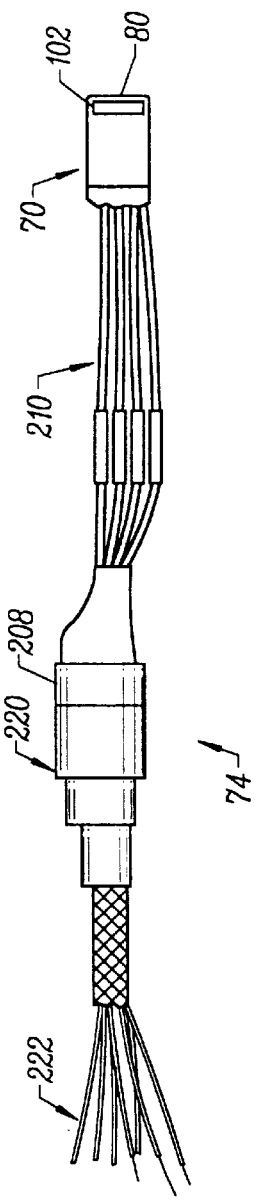
FIG. 5 illustrates the electrical connections and the electrode support of the handpiece in greater detail.

Referring now to FIGS. 2–5, an exemplary electrosurgical probe 10 comprises a shaft or disposable tip 13 removably coupled to a proximal handle 12, and an electrically insulating electrode support member 70 extending from tip 13 for supporting a plurality of electrode terminals 58 (see FIGS. 2 and 5). Tip 13 and handle 12 typically comprise a plastic material that is easily molded into a suitable shape for handling by the surgeon. As shown in FIGS. 3 and 5, handle 12 defines an inner cavity 72 that houses the electrical connections 74 (discussed below in reference to FIG. 5), and provides a suitable interface for connection to electrical connecting cable 34 (see FIG. 1). In the exemplary embodiment, handle 12 is constructed of a steam autoclavable plastic or metal (e.g., polyethylether keytone, or a stable metal alloy containing aluminum and/or zine. so that it can be re-used by sterilizing handle 12 between surgical procedures. High service temperature materials are preferred, such as a silicone cable jacket and a poly-ether-imide handpiece or ULTEM® that can withstand a repeated exposure to high temperatures.

Figure 4:
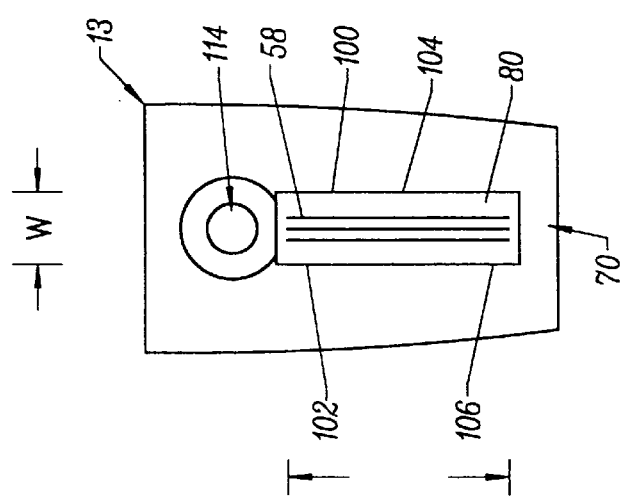
FIG. 4 is an end view of the distal tip of the probe, illustrating an electrode support with a plurality of electrode terminals.

Referring to FIGS. 4A–4C, tip 13 preferably comprises first and second housing halves 200, 202 that snap fit together, and form a recess 204 therebetween for holding electrode support member 70 within the tip 13. Electrode support member 70 extends from the distal end of tip 13 (usually about 0.5 to 20 mm), and provides support for a plurality of electrically isolated electrode terminals 58 and one or more return electrodes 100, 102 (see FIG. 4). Alternatively, electrode support member 70 may be recessed from the distal end of tip 13 to help confine the electrically conductive fluid around the electrode terminals 58 during the surgical procedure, as discussed above. Electrode support member 70 has a substantially planar tissue treatment surface 80 that is usually disposed at an angle of about 10 to 90 degrees relative to the longitudinal axis of handle 12 to facilitate handling by the surgeon. In the exemplary embodiment, this function is accomplished by orienting tip 13 at an acute angle relative to the longitudinal axis of handle 12.

In the embodiment shown in FIGS. 2–5, probe 10 includes first and second return electrodes 100, 102 for completing the current path between electrode terminals 58 and power supply 28 (see FIG. 1). As shown, return electrodes 100, 102 preferably have fluid contact surfaces on either lateral surface 104, 106 of electrode support member 70 slightly proximal to tissue treatment surface 80, typically about 0.1 to 2 mm, preferably about 0.2 to 1 mm. Return electrodes 100, 102 will usually have an exposed surface area of about 5 mm2 to 25 mm2, preferably about 18 mm2 to about 20 mm2. Return electrodes 100, 102 are coupled to a connector 104 (details of this connection discussed below) that extends to the proximal end of handle 13, where it is suitably connected to power supply 28 (FIG. 1).

Referring to FIGS. 4A–4C and FIG. 5, tip 13 further includes a proximal hub 206 for supporting a male electrical connector 208 that holds a plurality of wires 210 each coupled to one of the electrode terminals 58 and the return electrodes 100, 102 on support member 70 (see FIGS. 7–13 for details of the representative support member 70). A female connector 220 housed within handle 12 is removably coupled to male connector 208, and a plurality of wires 222 extend from female connector 220 through a strain relief 224 to cable 34. Both sets of wires 210, 222 are insulated to prevent shorting in the event of fluid ingress into the probe 10. This design allows for removable connection of the electrodes in tip 13 with the connector 220 within handle 12 so that the handle can be re-used with different tips 13. Probe 10 will preferably also include an identification element, such as a coded resistor (not shown), for programming a particular voltage output range and mode of operation for the power supply. This allows the power supply to be employed with a variety of different probes for a variety of different applications.

As shown in FIG. 5, return electrodes 100, 102 are not directly connected to electrode terminals 58. To complete this current path so that electrode terminals 58 are electrically connected to return electrodes 102, 100, electrically conducting fluid (e.g., isotonic saline or electrically conducting gel) is located between the active and return electrodes during a surgical procedure. In the representative embodiment, probe 10 includes a fluid tube 110 (FIG. 2) for delivering electrically conductive fluid to the target site. Fluid tube 110 is sized to extend through a groove 114 in handle 13 and through an inner cavity 112 (FIG. 3 and FIGS. 4A–4C) in tip 12 to a distal opening 114 (FIG. 4) located adjacent electrode support member 70. Tube 110 extends all the way through inner cavity 112 to opening 114 to eliminate any possible fluid ingress into cavity 112. As shown in FIGS. 1 and 2, fluid tube 110 includes a proximal connector 112 for coupling to an electrically conductive fluid source 21.

Probe 10 will also include a valve or equivalent structure for controlling the flow rate of the electrically conducting fluid to the target site. In the representative embodiment shown in FIGS. 4A–4C, handle 12 comprises a main body 130 coupled between distal hub 118 and strain relief 120, and a rotatable sleeve 116 around main body 130. Distal hub 118 has an opening 119 for receiving proximal hub 206 of tip 13 for removably coupling the tip 13 to the handle 12. Sleeve 116 is rotatably coupled to strain relief 120 and distal hub 118 to provide a valve structure for fluid tube 110. As shown in FIG. 2, fluid tube 110 extends through groove 114 from strain relief 120, through main body 130 and distal hub 120 to tip 13. Rotation of sleeve 116 will impede, and eventually obstruct, the flow of fluid through tube 110. Of course, this fluid control may be provided by a variety of other input and valve devices, such as switches, buttons, etc.

In alternative embodiments, the fluid path may be directly formed in probe by, for example, a central inner lumen or an annular gap (not shown) within the handle and the tip. This inner lumen may be formed near the perimeter of the probe 10 such that the electrically conducting fluid tends to flow radially inward towards the target site, or it may be formed towards the center of probe 10 so that the fluid flows radially outward. In addition, the electrically conducting fluid may be delivered from a fluid delivery element (not shown) that is separate from probe 10. In arthroscopic surgery, for example, the body cavity will be flooded with isotonic saline and the probe 10 will be introduced into this flooded cavity. Electrically conducting fluid will be continually resupplied to maintain the conduction path between return electrodes 100, 102 and electrode terminals 58. A more complete description of alternative electrosurgical probes incorporating one or more fluid lumen(s) can be found in U.S. Pat. No. 5,697,281, the complete disclosure of which has previously been incorporated herein by reference.

Referring to FIGS. 4 and 5, electrically isolated electrode terminals 58 are spaced apart over tissue treatment surface 80 of electrode support member 70. In the representative embodiment, the tissue treatment surface 80 has a rectangular cross-sectional shape with a length L in the range of about 0.5 mm to 20 mm (preferably about 2 to 10 mm) and a width W in the range from 0.3 mm to 10 mm (preferably about 0.5 to 4 mm). The individual electrode terminals 58 have the dimensions described above, and are preferably substantially flush with tissue treatment surface 80. Applicant has found that this configuration minimizes any sharp electrode edges and/or corners that would promote excessively high electric field intensities and associated current densities when a high frequency voltage is applied to the electrode terminals, thereby minimizing the rate of ablation as preferred for removing thin layers of tissue (e.g., epidermal layers).

It should be noted that the electrode terminals 58 may protrude slightly outward from surface 80, typically by a distance from 0 mm to 2 mm, or the terminals may be recessed from this surface. For example, the electrode terminals 58 may be recessed by a distance from 0.01 mm to 1 mm, preferably 0.01 mm to 0.2 mm. In one embodiment of the invention, the electrode terminals are axially adjustable relative to the tissue treatment surface so that the surgeon can adjust the distance between the surface and the electrode terminals.

Referring now to FIGS. 7–13, an exemplary electrode support member 70 will be described in detail. As shown, electrode support member 70 preferably comprises a multilayer substrate comprising a suitable high temperature, electrically insulating material, such as ceramic. The multilayer substrate is a thin or thick-film hybrid having conductive strips that are adhered to the ceramic wafer layers (e.g., thick-film printed and fired onto or plated onto the ceramic wafers). The conductive strips typically comprise tungsten, gold, nickel, silver, platinum or equivalent materials. In the exemplary embodiment, the conductive strips comprise gold, and they are co-fired together with the wafer layers to form an integral package. The conductive strips are coupled to external wire connectors by holes or vias that are drilled through the ceramic layers, and plated or otherwise covered with conductive material.

Figure 9A:
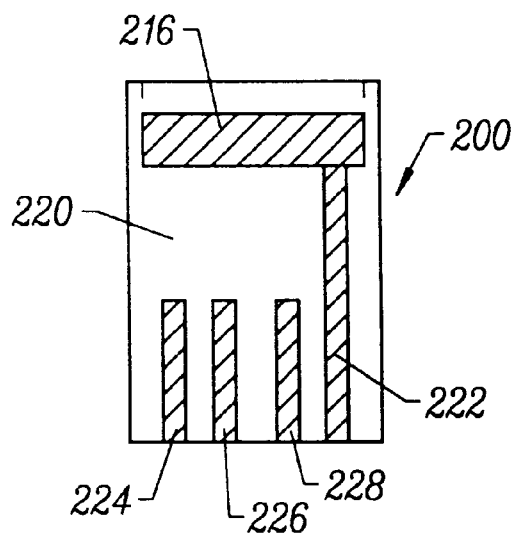
Figure 9B:
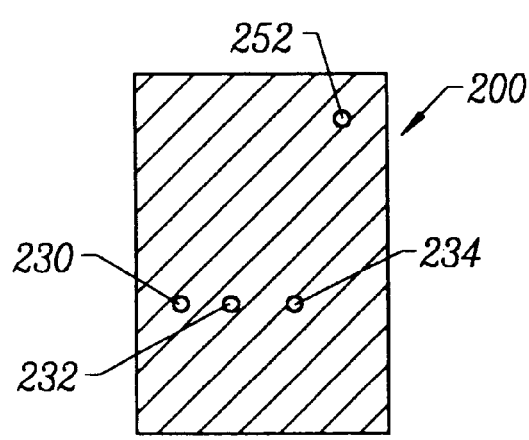

In the representative embodiment, support member 70 comprises five ceramic layers 200, 202, 204, 206, 208 (see FIGS. 9–13), three gold plated electrode terminals 210, 212, 214 and first and second gold plated return electrodes 216, 218. As shown in FIGS. 8A, 9A and 9B, a first ceramic layer 200, which is one of the outer layers of support 70, includes first gold plated return electrode 216 on a lateral surface 220 thereof. First ceramic layer 200 further includes a gold conductive strip 222 extending from return electrode 216 to the proximal end of the layer 200 for coupling to a lead wire (not shown), and three gold conductive lines 224, 226, 228 extending from a mid-portion of the layer 200 to its proximal end. Conductive strips 224, 226, 228 are each coupled to one of the electrode terminals 210, 212, 214 by conductive holes or vias 230, 232, 234, respectively. As shown, all three vias 230, 232, 234 extend through wafer layer 200.

Figure 10A:
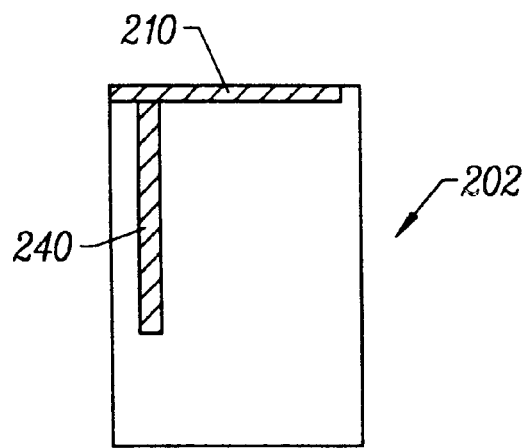
Figure 10B:
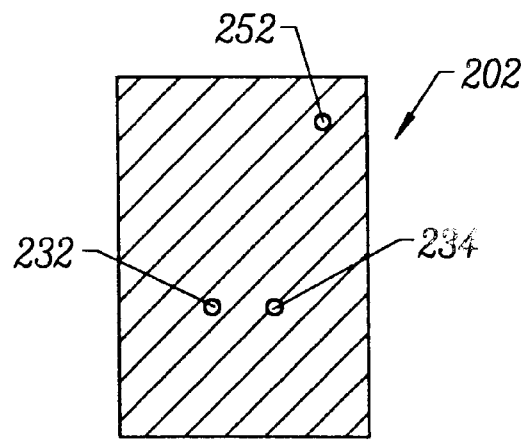
Figure 13:
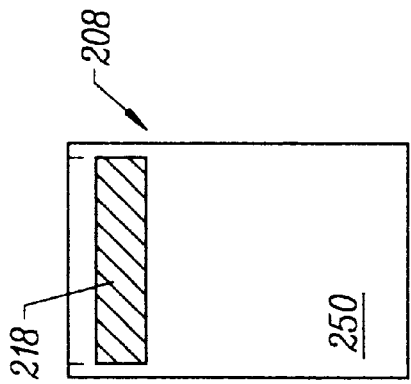
Figure 12A:
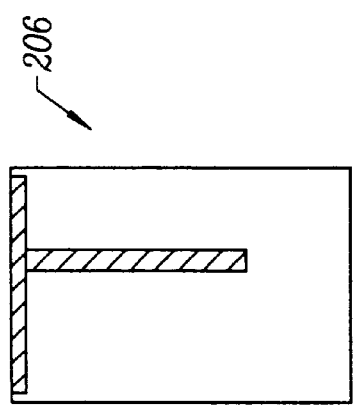
Figure 12B:
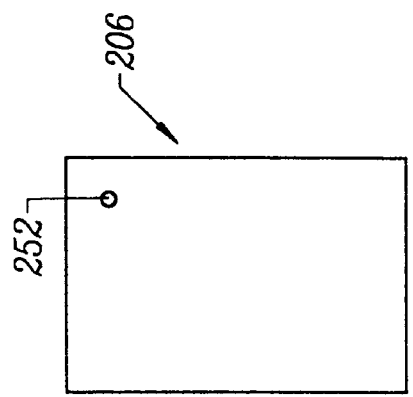
Figure 11A:
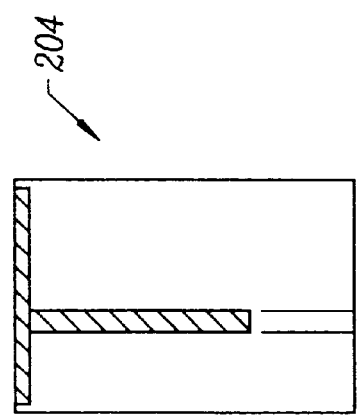
Figure 11B:
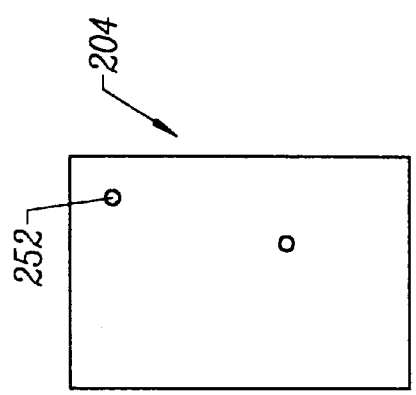

Referring to FIGS. 10A and 10B, a second wafer layer 202 is bonded between the outer wafer layer 200 and a middle wafer layer 204 (FIGS. 11A and 11B). As shown, first electrode terminal 210 is attached to the distal surface of second wafer layer 202, and a conductive strip 240 extends to via 230 to couple electrode terminal 210 to a lead wire. Similarly, wafer layers 204 and 206 (FIGS. 11 and 12) each have an electrode terminal 212, 214 plated to their distal surfaces, and a conductive strip 242, 244, respectively, extending to one of the vias 232, 234, respectively. Note that the vias only extend as far as necessary through the ceramic layers. As shown in FIG. 13, another outer wafer layer 208 has a second return electrode 218 plated to the lateral surface 250 of layer 208. The second return electrode 218 is coupled directly to the first return electrode 216 through a via 252 extending through the entire ceramic substrate.

Figure 14:
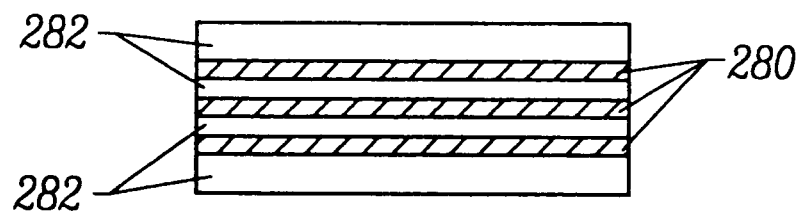
FIGS. 14 and 15 illustrate an alternative multi-layer wafer design according to the present invention.
Figure 15:
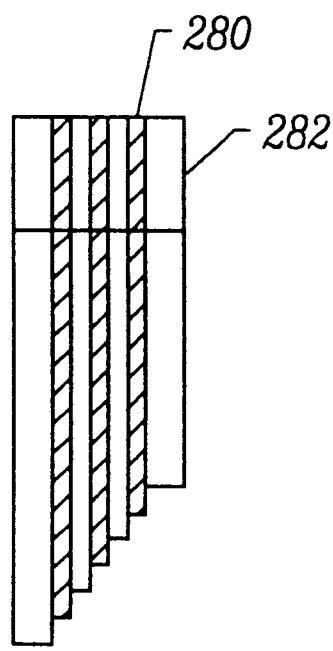

Of course, it will be recognized that a variety of different types of multilayer wafers may be constructed according to the present invention, For example, FIGS. 14 and 15 illustrate an alternative embodiment of the multilayer ceramic wafer, wherein the electrode terminals comprise planar strips 280 that are plated or otherwise bonded between the ceramic wafer layers 282 . Each of the planar strips 280 has a different length, as shown in FIG. 15, so that the electrode terminals can be electrically isolated from each other, and coupled to lead wires by vias (not shown).

Figure 16A:
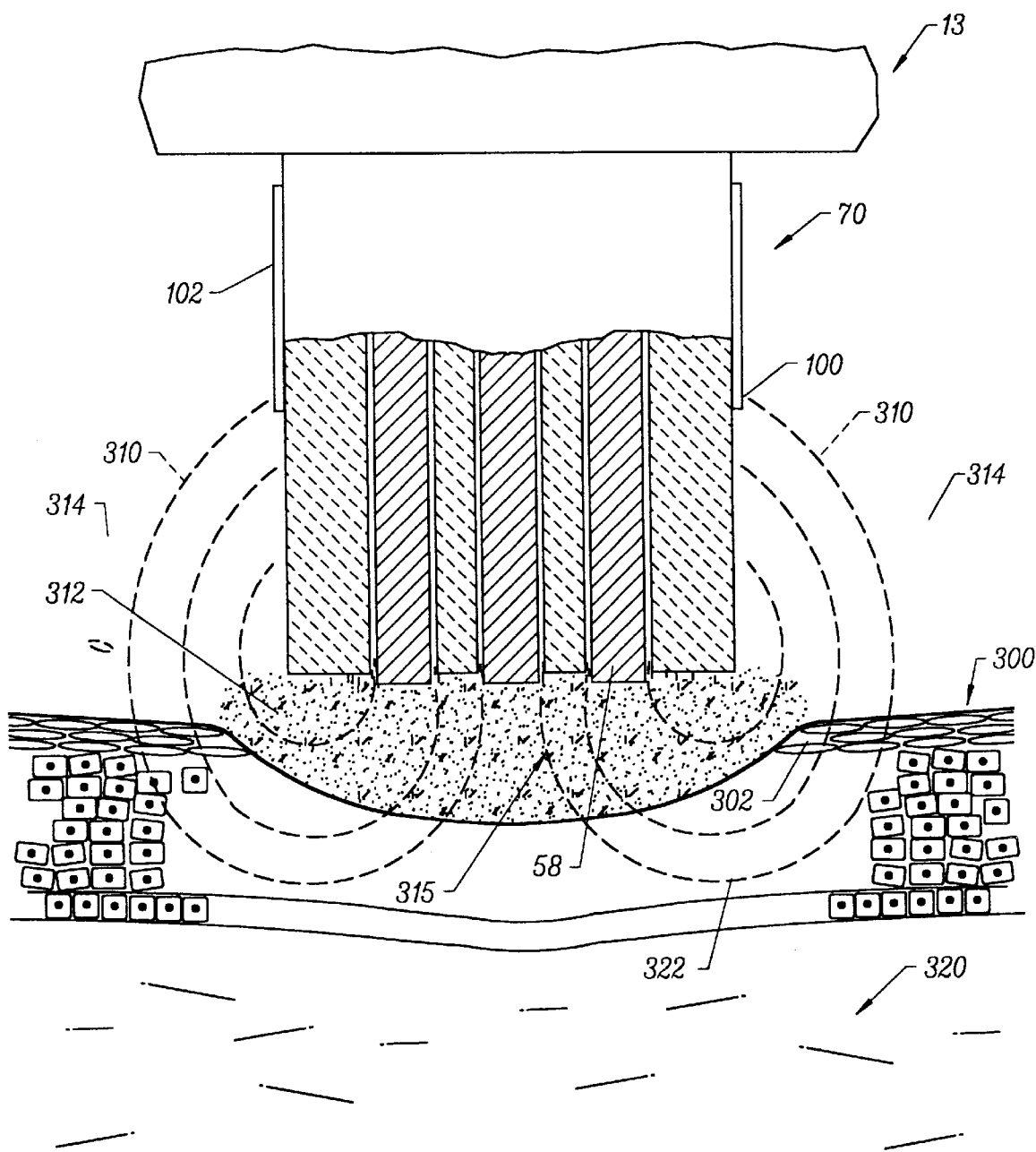
FIG. 16A illustrates a method for treating the outer layer of a patient's skin in a skin resurfacing procedure, wherein an outer layer of epidermis is removed or ablated and the collagen fibers in the underlying dermis are contracted.
Figure 16B:
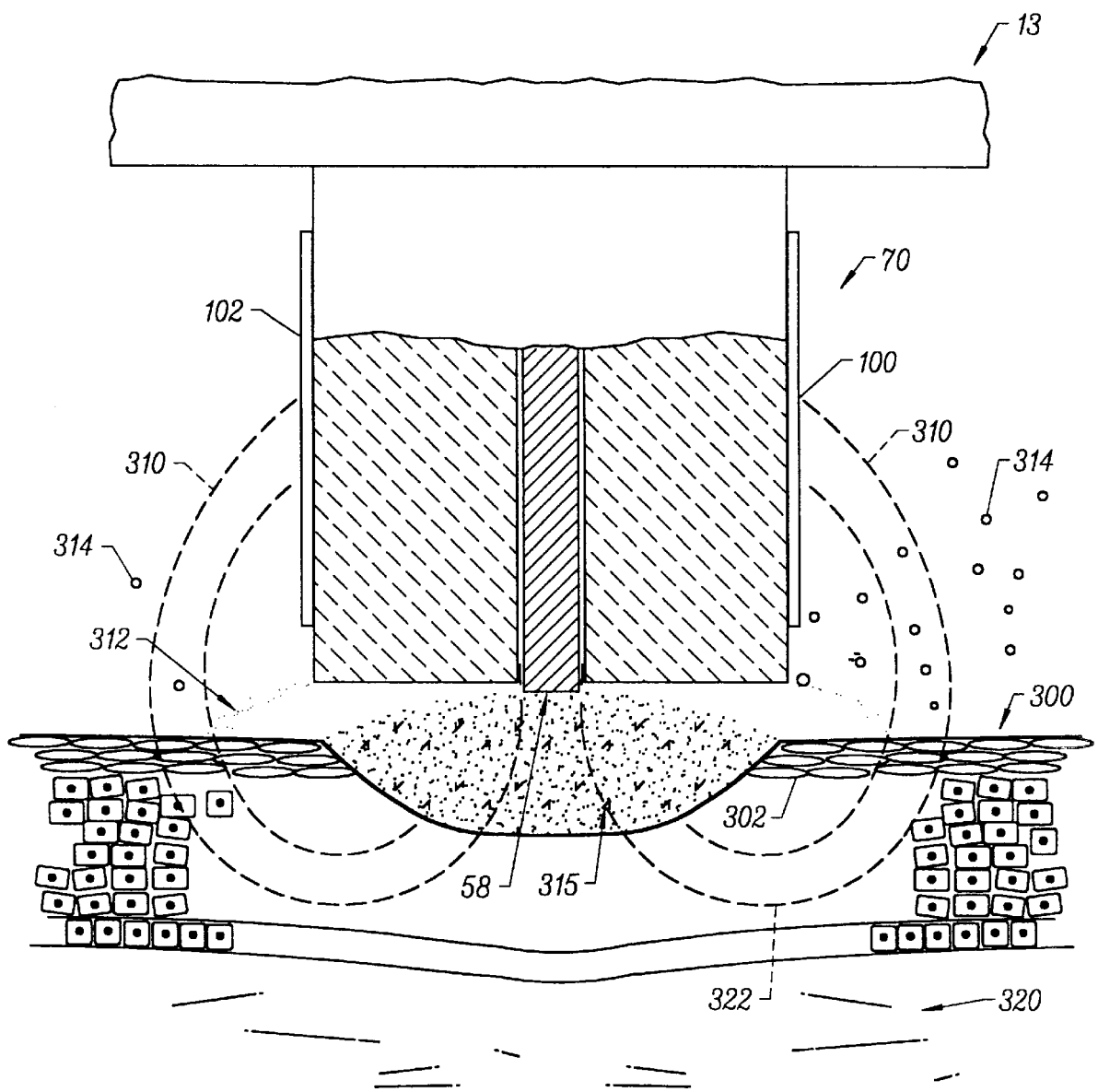
FIG. 16B illustrates a illustrates a method for treating the outer layer of a patient's skin in a skin resurfacing procedure with an electrosurgical probe having a single, active electrode terminal.

Referring now to FIGS. 16A and 16B, a method of treating tissue on the outer skin of a patient according to the present invention will now be described. As shown, distal tip 13 of probe 10 is positioned such that electrode support 70 is adjacent to the target tissue 302 at the treatment site 300. Electrically conducting fluid 304 is delivered through fluid tube 110 (FIG. 2) through distal hole 114 to the treatment site 300. The rate of fluid flow is controlled with rotatable sleeve 116 (FIG. 4A) such that the zone between the tissue 302 and electrode support 70 is constantly immersed in the fluid. The power supply 28 is then turned on and adjusted such that a high frequency voltage difference is applied between electrode terminal(s) 58 and return electrodes 100, 102. The electrically conductive fluid 304 provides the conduction path (see current flux lines 310) between electrode terminal (s) 58 and the return electrodes 100, 102 on either side of electrode support 70.

In the exemplary embodiment, the high frequency voltage is sufficient to convert the electrically conductive fluid 304 between the target tissue 302 and electrode terminals 58 into an ionized vapor layer 312 or plasma. As a result of the applied voltage difference between electrode terminals 58 and the target tissue 302 (i.e., the voltage gradient across the plasma layer 312), charged particles 315 in the plasma (viz., electrons) are accelerated towards the tissue. At sufficiently high voltage differences, these charged particles 315 gain sufficient energy to cause dissociation of the molecular bonds within tissue structures. This molecular dissociation is accompanied by the volumetric removal (i.e., ablative sublimation) of tissue and the production of low molecular weight gases 314, such as oxygen, nitrogen, carbon dioxide, hydrogen and methane. The short range of the accelerated charged particles 315 within the target tissue 302 confines the molecular dissociation process to the surface layer to minimize damage and necrosis to the underlying tissue 320.

In some embodiments, the voltage difference will be sufficient enough to apply thermal energy to the underlying tissue 320. Preferably, this thermal energy will be sufficient to elevate the tissue temperature from normal body temperatures (e.g., 37° C.) to temperatures in the range of 45° C. to 90° C., preferably in the range from 55° C. to 70° C. and, for the case of skin, preferably in the range of about 55° C. to 62° C. This temperature elevation causes contraction of the collagen connective fibers within the underlying tissue 320. This method removes the surface layer of the skin, while tightening the underlying dermis to remove wrinkles and rejuvenate the skin.

Figure 17:
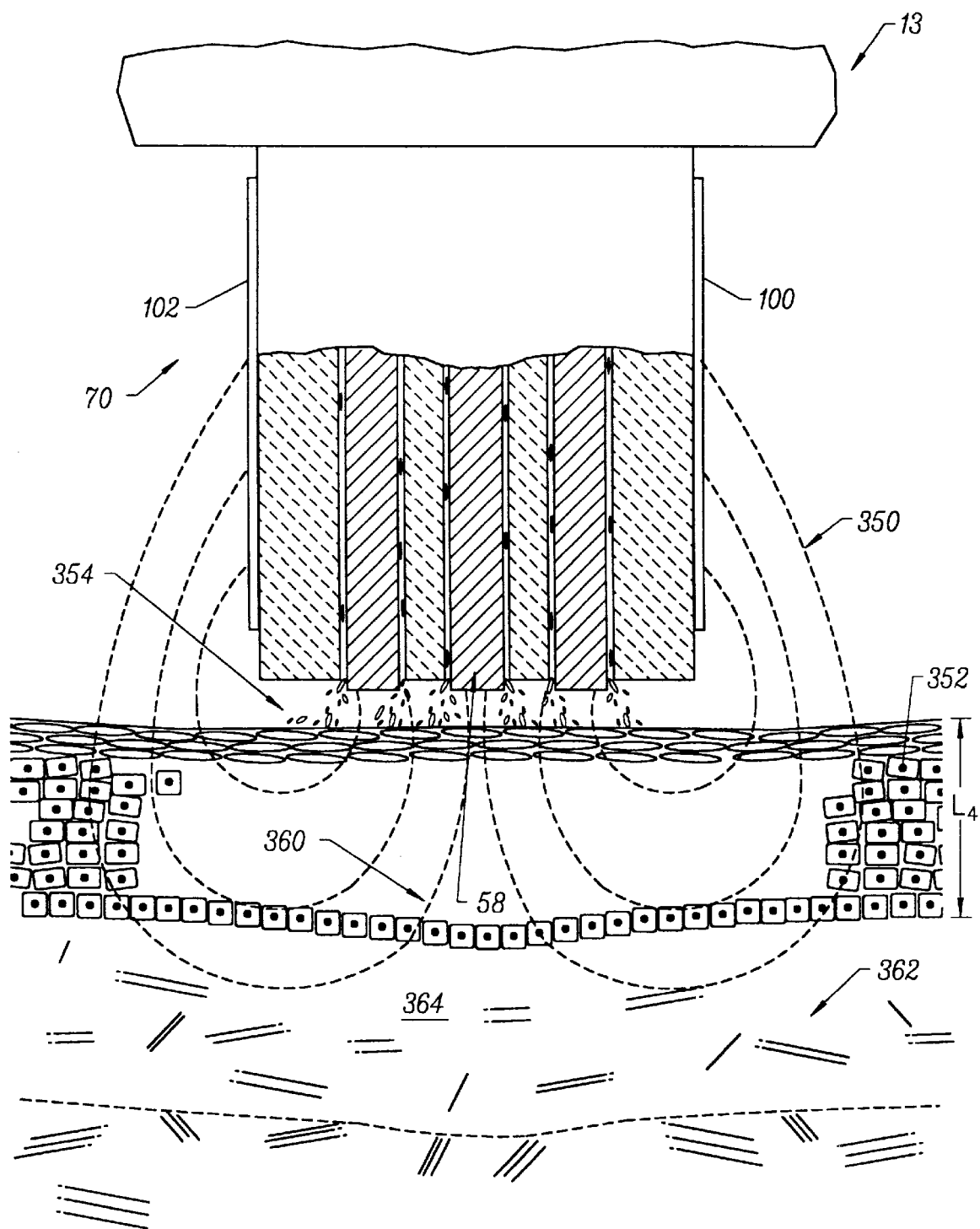
FIG. 17 illustrates a method of skin resurfacing wherein the epidermal layer is separated from the papillary dermis, and then removed by wiping away the separated layer.

An alternative method for skin rejuvenation or wrinkle removal is shown in FIG. 17. In this method, when a voltage difference is applied between the electrode terminals 58 and the return electrodes 100, 102, electrical current flows between the electrode terminals 58 and the return electrode 100, 102 along current flux lines 350. The current flux lines 350 flow a short distance, $L_4$ into the surface of epidermal tissue 352 and through the electrically conductive fluid 354 in the region above the surface of the tissue to complete the electrical path between the electrode terminals 58 and the return electrodes 100, 102. As a consequence of the electrical impedance of the tissue and the proper selection of the applied frequency, voltage and current, heating of the epidermal tissue 352 occurs in a region 360 below the surface of the tissue 352. This heating elevates the temperature of the tissue and separates the epidermal tissue layer 352 from the underlying papillary dermis 362. The epidermal tissue layer 352 may then be removed by flushing the treatment site, or by brushing away this tissue layer 352 with, for example, a cloth pad, gauze, etc. In skin rejuvenation procedures, collagen may be injected into the dermis after the epidermis has been removed to rejuvenate skin that has lost its elasticity.

In addition, the heating from current flux lines 350 may be sufficient to elevate the temperature of the tissue 364 in the papillary dermis 362 from normal body temperature (e.g. 37° C.) to a temperature in the range 55° C. to 85° C., preferably in the range from 60° C. to 70° C. This heating of the papillary dermis 362 will cause irreversible contraction of the collagen with the papillary dermis.

Figure 18A:
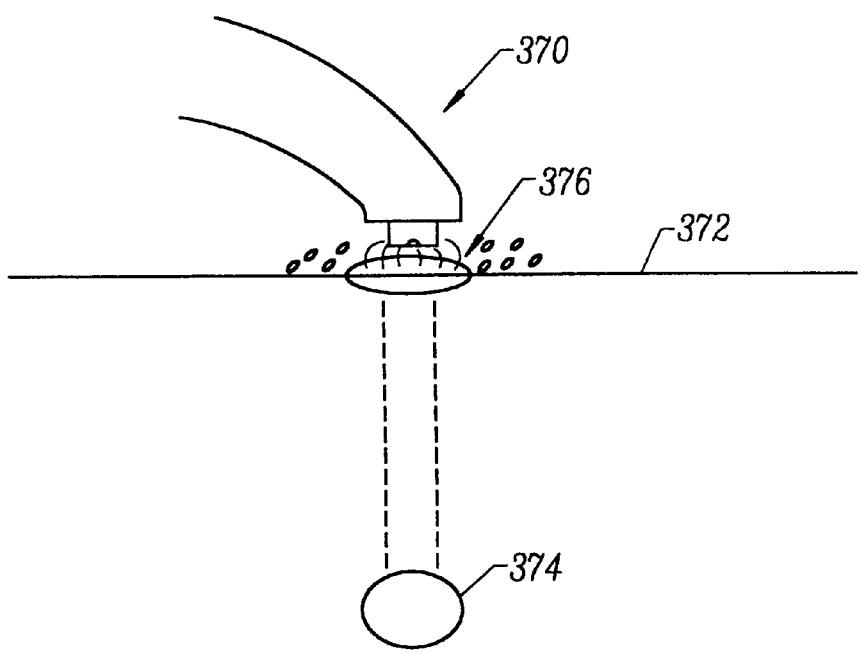
FIGS. 18A and 18B illustrate a method for treating a vascular lesion.
Figure 18B:
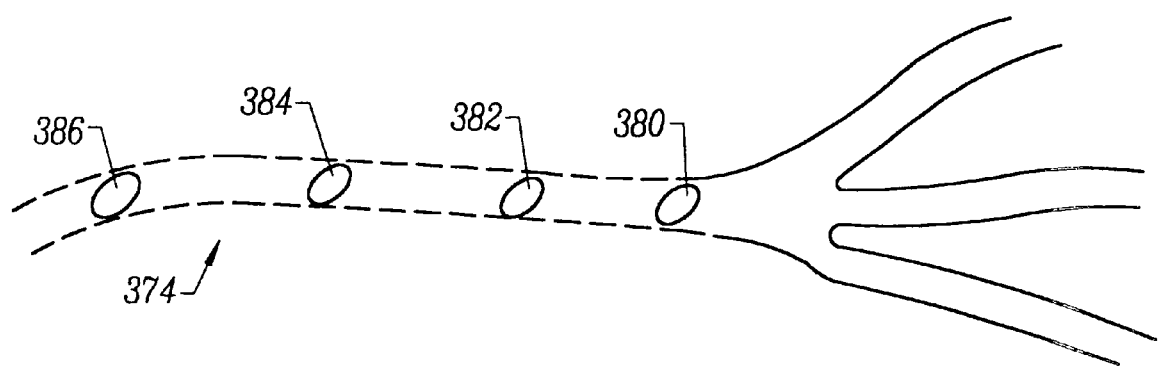

FIGS. 18A and 18B illustrate a method for treating a vascular lesion, such as a port wine stain, face vein, birth mark or the like. As shown in FIG. 18A, an electrosurgical probe 370 is placed on or adjacent to the surface of the skin 372 above the vessel 374 to be treated. A voltage difference is applied between the active and return electrodes (not shown) in the presence of electrically conductive fluid 376 to ablate or cause molecular dissociation of the tissue adjacent the probe 370. As the tissue is removed, the probe will be axially translated through the deepening hole to the vessel 374 (note that a substantially linear probe shaft is preferred in this embodiment). A more complete description of systems and methods for forming channels or holes through tissue is described in commonly assigned, U.S. Pat. No. 5,683,366, the complete disclosure of which is incorporated herein by reference. Once the probe approaches the vessel, thermal energy will be delivered into the vessel from the current flux lines as described above. This thermal energy will eventually be sufficient to coagulate the blood in the vessel 374 and collapse the vessel at that site.

In order to collapse a long length of the vessel 374, multiple treatment sites may be necessary. As shown in FIG. 18B, it is desirable to locate the first treatment site 380 at a downstream point with respect to the flow of blood in the vessel. The surgeon may then sequentially treat the vessel at multiple sites (382, 384, 386) upstream from the first site 380.

Figure 19:
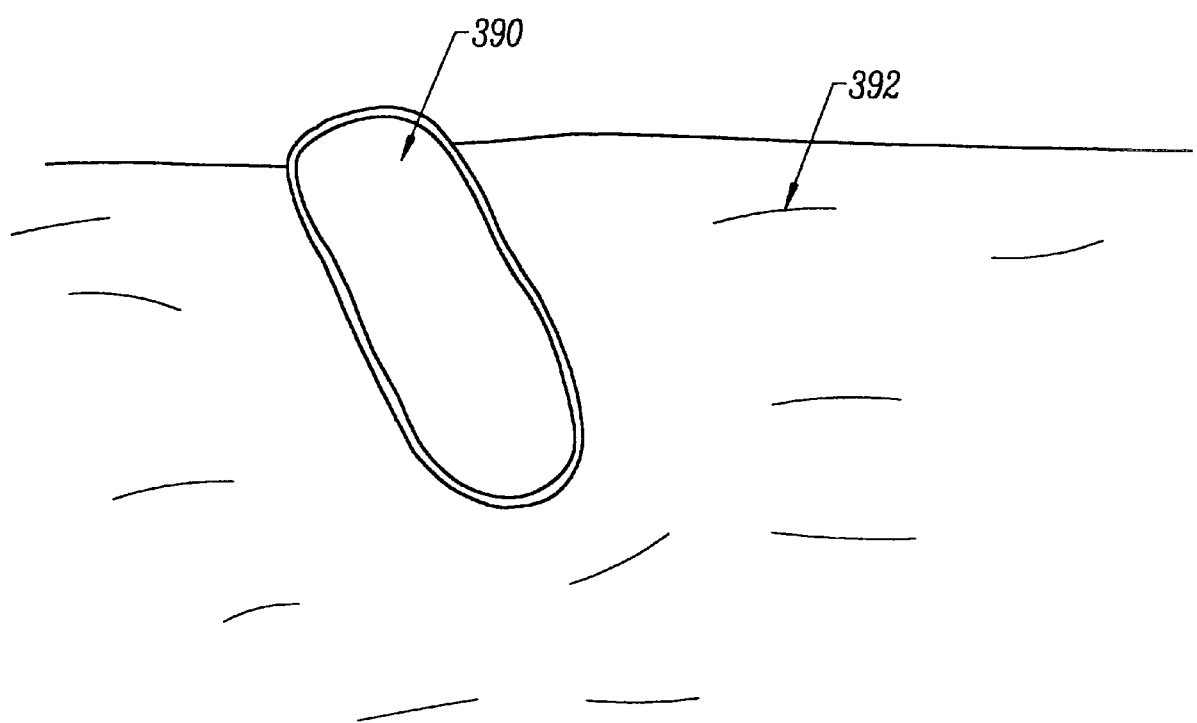
FIG. 19 illustrates a method of removing scalp tissue and/or hair according to the present invention.

Referring now to FIG. 19, a method for transplanting hair according to the present invention is described. A strip of hair (not shown) from a donor region is first excised from the patient. The hair may be excised by removing the tissue around the strip in a similar manner as described above. The hemostatic effects of the electrosurgical system of the present invention result in minimal bleeding at the donor site. The strip is then lifted from the scalp and sutures are used to close the opening.

One of the probes described above are then used to produce incisions 390 in the recipient area 392. As shown in FIG. 19, the depth an diameter of the incision 390 can be accurately controlled. The incisions are preferably formed at an angle to improve the retention of the graft and to form a more cosmetically suitable appearance.

Figure 20:
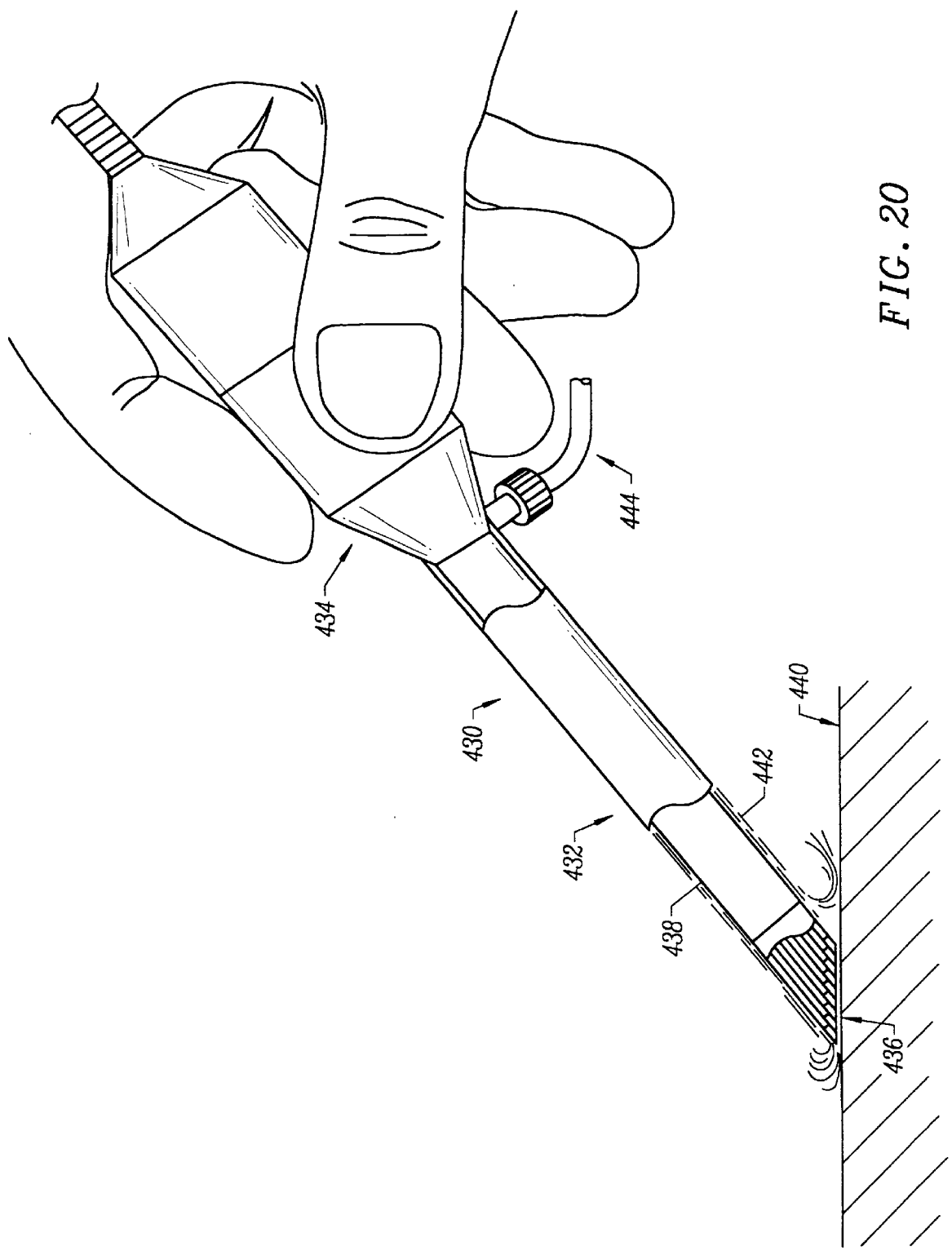
FIG. 20 is a cross-sectional view of an alternative electrosurgical probe for applying high frequency voltage to tissue layers on the skin.

FIG. 20 illustrates an alternative embodiment, where an electrosurgical probe 430 is utilized to remove the surface layers of the epidermis 440. Probe 430 includes a shaft 432 coupled to a proximal handle 434 for holding and controlling shaft 432. Similar to previous embodiments, probe 430 includes an active electrode array 436 at the distal tip of shaft 432, an annular return electrode 438 extending through shaft 432 and proximally recessed from the active electrode array 436 and an annular lumen 442 between return electrode 438 and an outer insulating sheath 444. Probe 430 further includes a liquid supply conduit 446 attached to handle 434 and in fluid communication with lumen 442 and a source of electrically conducting fluid (not shown) for delivering the fluid past return electrode 438 to the target site on the epidermis 440. As discussed above, electrode array 436 is preferably flush with the distal end of shaft 432 or distally extended from the distal end by a small distance (on the order of 0.005 inches) so to minimize the depth of ablation. Preferably, the distal end of shaft 432 is beveled to improve access and control of probe 430 while treating the epidermal tissue.

Figure 22:
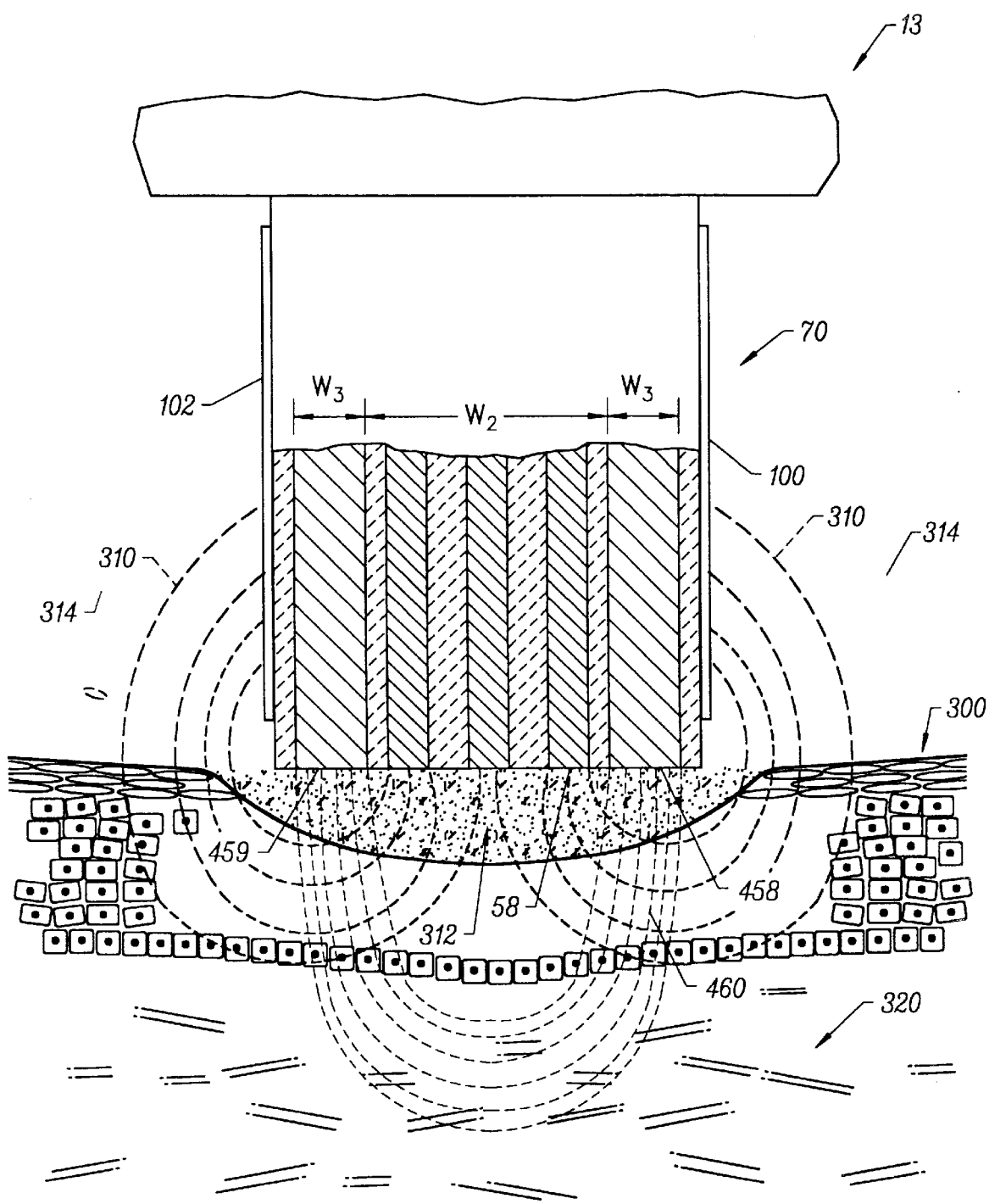
FIG. 22 illustrates another embodiment of the probe of the present invention, incorporating additional electrodes sized for contraction of tissue.

Yet another embodiment of the present invention is shown in FIG. 22. This embodiment is similar to that shown in FIG. 16 and described above with the exception that additional electrode terminals 458, 459 are positioned at the distal tip 70 of the probe. Electrode terminals 458, 459 may be the same size as ablation electrode terminals 58, larger as shown in FIG. 22. One operating arrangement is to connect electrode terminals 458, 459 to two poles of a high frequency generator to form a bipolar circuit allowing current to flow between terminals 458, 459 as shown by current flux lines 461. The electrode terminals 458, 459 are electrically isolated from ablation electrodes 58. By proper selection of the interelectrode spacing, $W_2$, and electrode width, $W_3$, and the frequency, the current flux lines 461 can be caused to flow below the epidermis layer to effect collagen shrinkage in region 320 as described hereinabove.

The voltage will preferably be sufficient to establish high electric field intensities between the active electrode array 436 and the epidermal tissue 440 to thereby induce molecular breakdown or disintegration of several cell layers of the epidermal tissue. As described above, a sufficient voltage will be applied to develop a thin layer of vapor within the electrically conducting fluid and to ionize the vaporized layer or region between the active electrode(s) and the target tissue. Energy in the form of photons and/or energetic electrons are discharged from the vapor layer to ablate the epidermal tissue, thereby minimizing necrosis of surrounding tissue and underlying cell layers, such as cell structures in the stratum lucidium and/or stratum granulosum.

Figure 23:
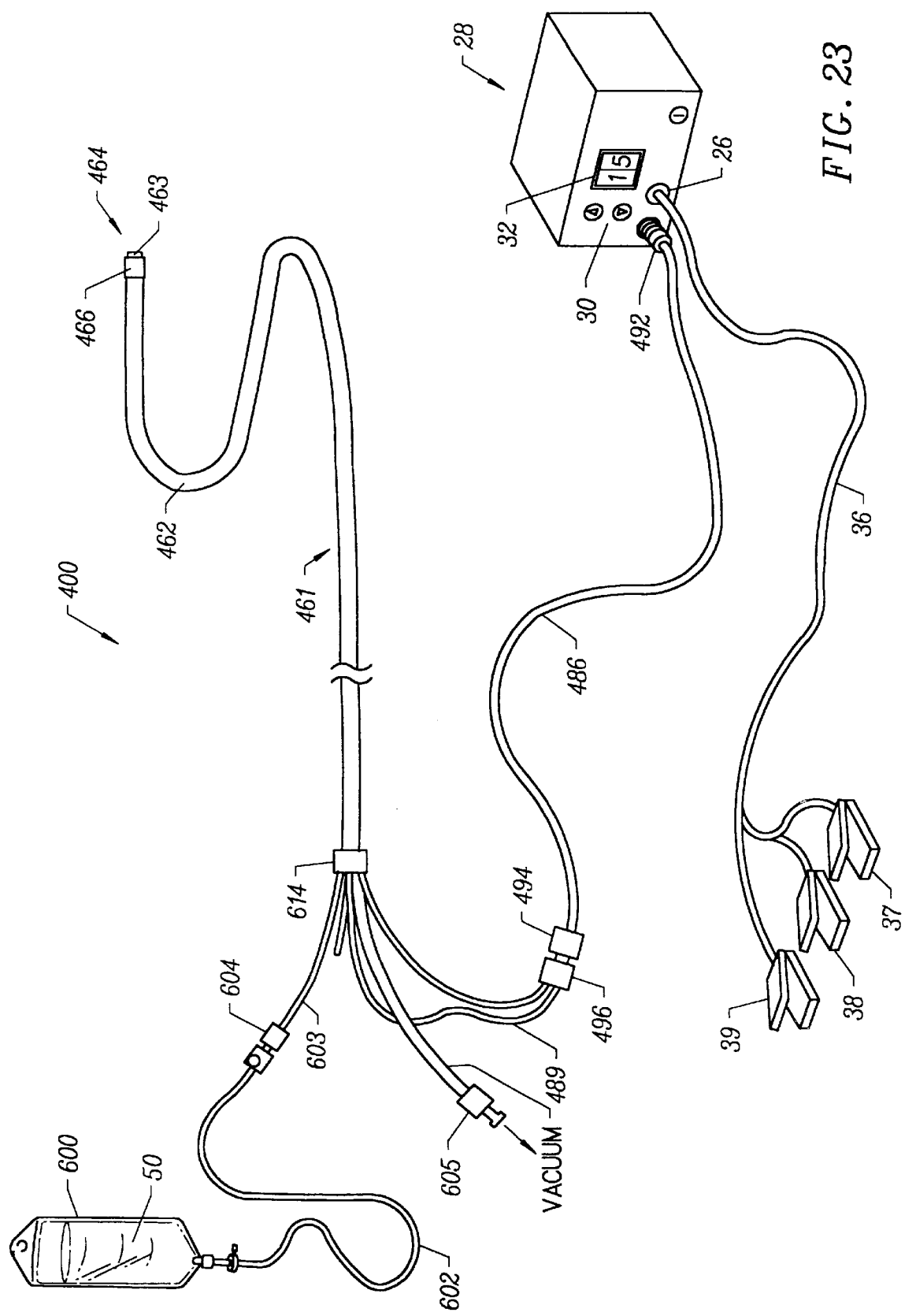
FIG. 23 is a perspective view of an electrosurgical catheter system for treating vascular disorders, such as aneurysms or vascular malformations, according to the present invention.
Figure 24:
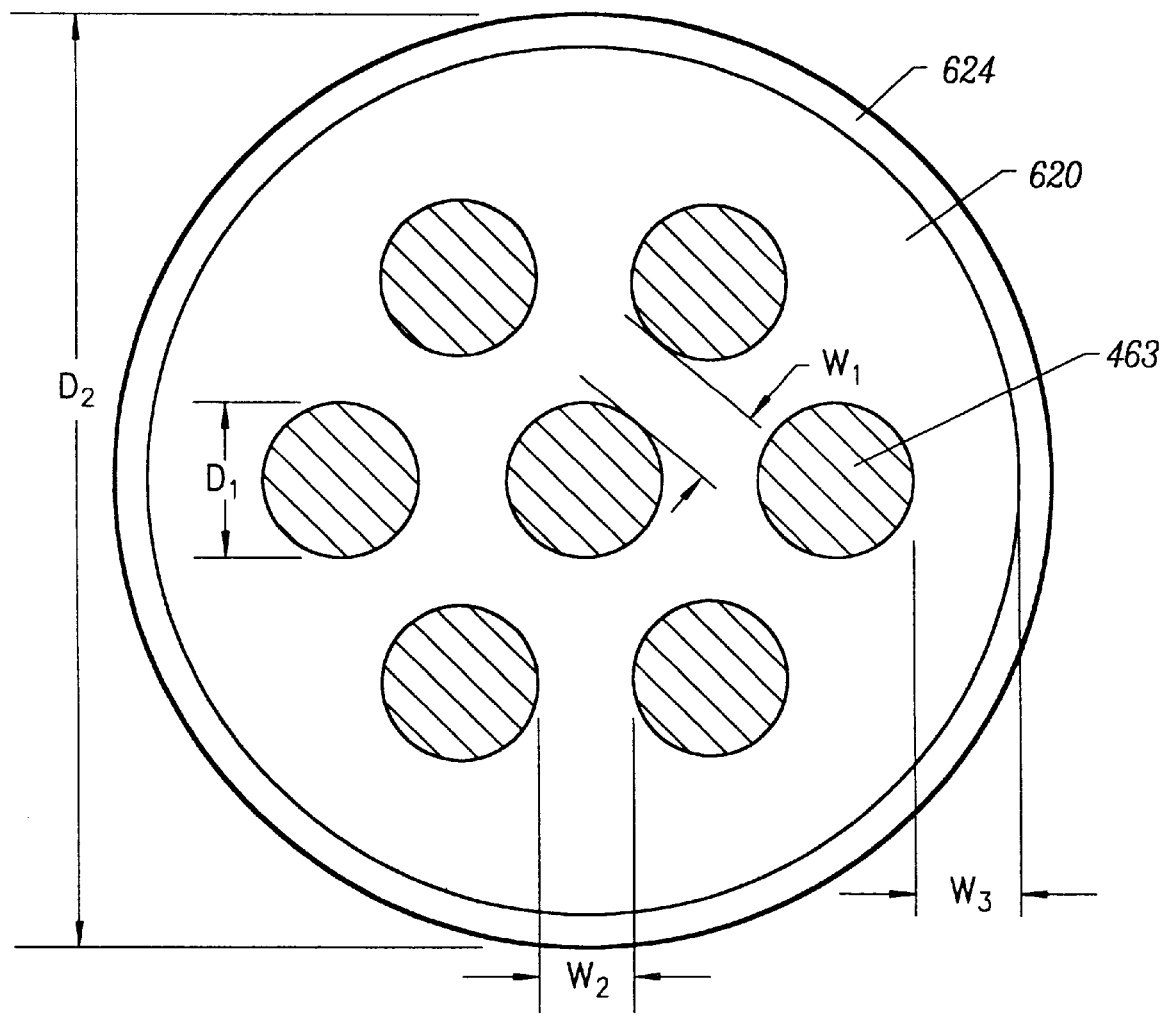
FIG. 24 illustrates the distal portion of an electrosurgical catheter for use with the system of FIG. 23.

Referring to FIGS. 23–25, the electrosurgical device according to the present invention may also be configured as an elongate catheter system 400 including portions with sufficient flexibility to permit introduction into the body and to the target site through one or more vascular lumen(s). In this embodiment, the catheter system of the present invention is particularly useful for treating vascular disorders, such as aneurysms, vascular malformations and the like, by causing sufficient thermal injury to an inner vessel wall to occlude or partially occlude the vessel lumen. As shown in FIG. 23, a catheter system 400 generally comprises an electrosurgical catheter 461 connected to a power supply 28 by an interconnecting cable 486 for providing high frequency voltage to a target tissue site and an irrigant reservoir or source 600 for providing electrically conducting fluid to the target site. Catheter 461 generally comprises an elongate, flexible shaft body 462 including a tissue removing or ablating region 464 at the distal end of body 462. The proximal portion of catheter 461 includes a multi-lumen fitment 614 which provides for interconnections between lumens and electrical leads within catheter 461 and conduits and cables proximal to fitment 614. By way of example, a catheter electrical connector 496 is removably connected to a distal cable connector 494 which, in turn, is removably connectable to generator 28 through connector 492. One or more electrically conducting lead wires (not shown) within catheter 461 extend between one or more active electrodes 463 at tissue ablating region 464 and one or more corresponding electrical terminals (also not shown) in catheter connector 496 via active electrode cable branch 487. Similarly, one or more return electrodes 466 at tissue ablating region 464 are coupled to a return electrode cable branch 489 of catheter connector 496 by lead wires (not shown). Of course, a single cable branch (not shown) may be used for both active and return electrodes.

Catheter body 462 may include reinforcing fibers or braids (not shown) in the walls of at least the distal ablation region 464 of body 462 to provide responsive torque control for rotation of electrode terminals during tissue engagement. This rigid portion of the catheter body 462 preferably extends only about 7 to 10 mm while the remainder of the catheter body 462 is flexible to provide good trackability during advancement and positioning of the electrodes adjacent target tissue.

Conductive fluid 50 is provided to tissue ablation region 464 of catheter 461 via a lumen (not shown in FIG. 23) within catheter 461. Fluid is supplied to lumen from the source along a conductive fluid supply line 602 and a conduit 603, which is coupled to the inner catheter lumen at multi-lumen fitment 614. The source of conductive fluid (e.g., isotonic saline) may be an irrigant pump system (not shown) or a gravity-driven supply, such as an irrigant reservoir 600 positioned several feet above the level of the patient and tissue ablating region 8. A control valve 604 may be positioned at the interface of fluid supply line 602 and conduit 603 to allow manual control of the flow rate of electrically conductive fluid 30. Alternatively, a metering pump or flow regulator may be used to precisely control the flow rate of the conductive fluid.

System 400 further includes an aspiration or vacuum system (not shown) to aspirate liquids and gases from the target site. The aspiration system will usually comprise a source of vacuum coupled to fitment 614 by a aspiration connector 605.

FIGS. 24 and 25 illustrate the working end 464 of an electrosurgical catheter 461 constructed according to the principles of the present invention. As shown in FIG. 11, catheter 461 generally includes an elongated shaft 462 which may be flexible or rigid, and an electrode support member 620 coupled to the distal end of shaft 462. Electrode support member 620 extends from the distal end of shaft 462 (usually about 1 to 20 mm), and provides support for a plurality of electrically isolated electrode terminals 463. Electrode support member 620 and electrode terminals 463 are preferably secured to a tubular support member 626 within shaft 461 by adhesive 630.

The electrode terminals 463 may be constructed using round, square, rectangular or other shaped conductive metals. By way of example, the electrode terminal materials may be selected from the group including stainless steel, tungsten and its alloys, molybdenum and its alloys, titanium and its alloys, nickel-based alloys, as well as platinum and its alloys. Electrode support member 620 is preferably a ceramic, glass or glass/ceramic composition (e.g., aluminum oxide, titanium nitride). Alternatively, electrode support member 620 may include the use of high-temperature biocompatible plastics such as polyether-ether-keytone (PEEK) manufactured by Vitrex International Products, Inc. or polysulfone manufactured by GE Plastics. The adhesive 630 may, by way of example, be an epoxy (e.g., Master Bond EP42HT manufactured by Master Bond) or a silicone-based adhesive.

Figure 25A:
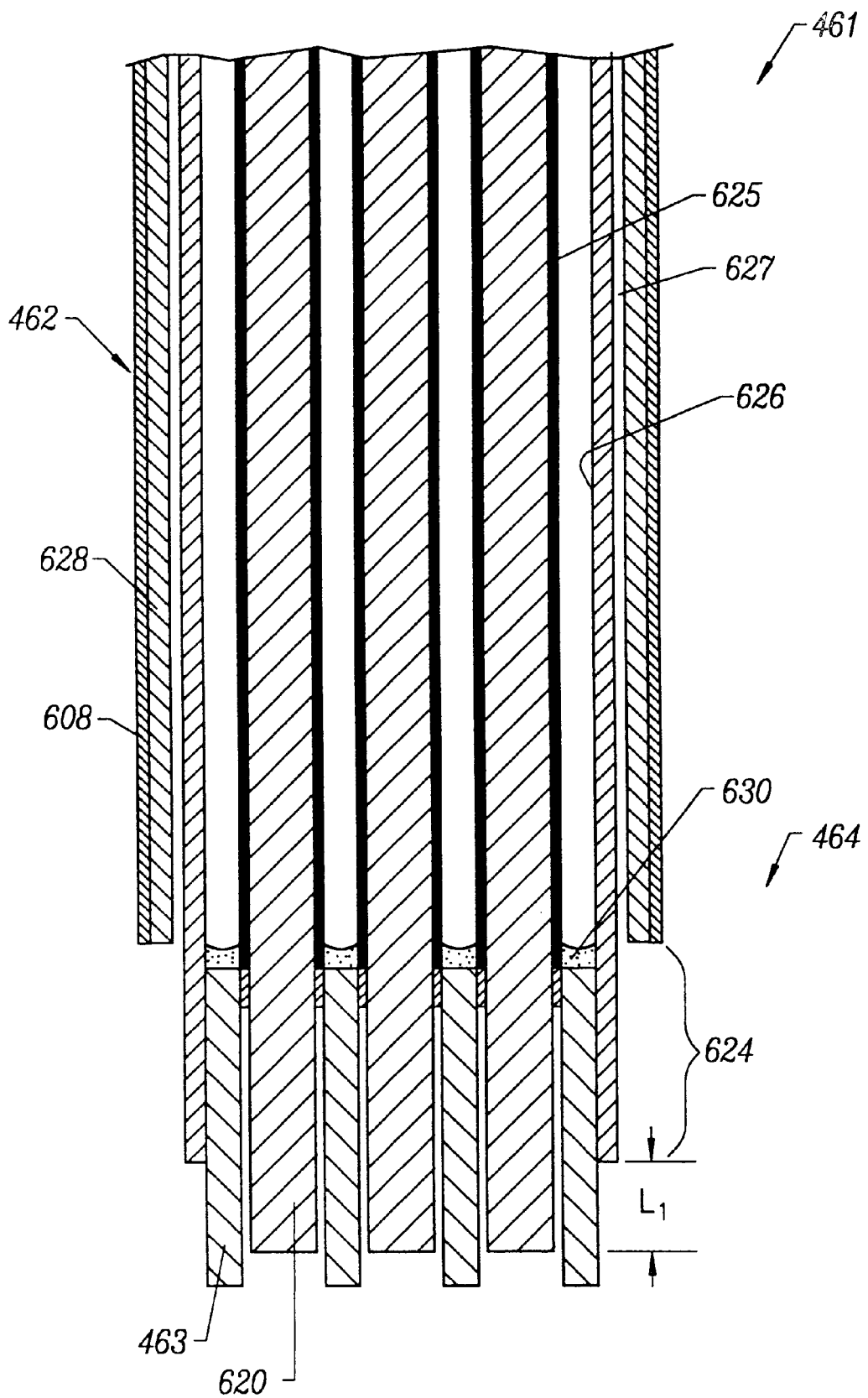
FIGS. 25A and 25B are cross-sectional and end views, respectively of a distal portion of a second electrosurgical catheter according to the present invention.
Figure 25B:
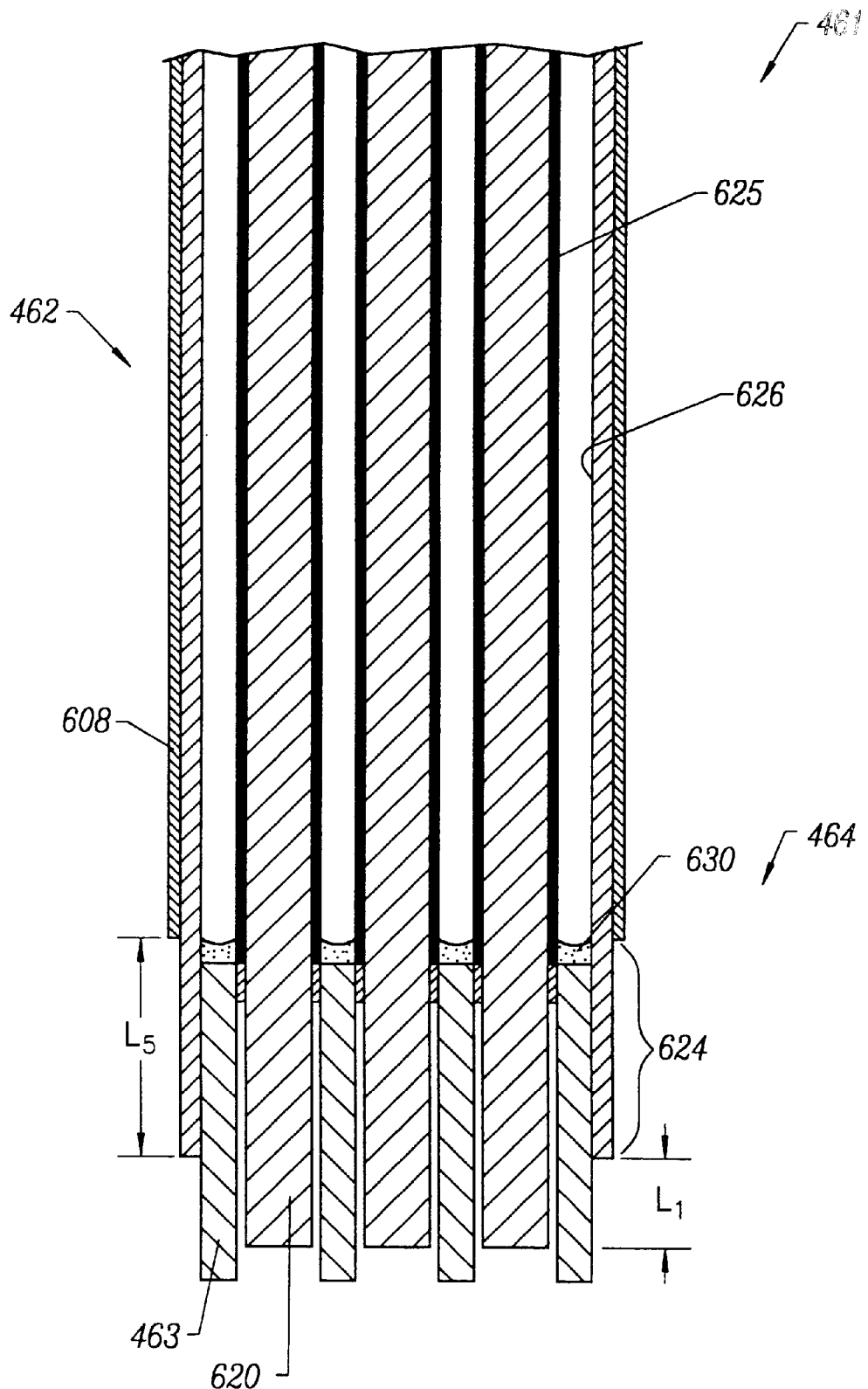

As shown in FIG. 25B, a total of 7 circular active electrodes or electrode terminals 463 are shown in a symmetrical pattern having an active electrode diameter, $D_1$ in the range from 0.05 mm to 1.5 mm, more preferably in the range from 0.1 mm to 0.75 mm. The interelectrode spacings, $W_1$ and $W_2$ are preferably in the range from 0.1 mm to 1.5 mm and more preferably in the range from 0.2 mm to 0.75 mm. The distance between the outer perimeter of the electrode terminal 463 and the perimeter of the electrode support member, $W_3$ is preferably in the range from 0.1 mm to 1.5 mm and more preferably in the range from 0.2 mm to 0.75 mm. The overall diameter, $D_2$ of the working end 464 of catheter body 462 is preferably in the range from 0.5 mm to 10 mm and more preferably in the range from 0.5 mm to 5 mm. As discussed above, the shape of the active electrodes may be round, square, triangular, hexagonal, rectangular, tubular, flat strip and the like and may be arranged in a circularly symmetric pattern as shown in FIG. 25B or may, by way of example, be arranged in a rectangular pattern, square pattern, or strip.

Catheter body 462 includes a tubular cannula 626 extending along body 462 radially outward from support member 620 and electrode terminals 463. The material for cannula 626 may be advantageously selected from a group of electrically conductive metals so that the cannula 626 functions as both a structural support member for the array of electrode terminals 463 as well as a return electrode 624. The support member 626 is connected to an electrical lead wire (not shown) at its proximal end within a connector housing (not shown) and continues via a suitable connector to power supply 28 to provide electrical continuity between one output pole of high frequency generator 28 and said return electrode 624. The cannula 626 may be selected from the group including stainless steel, copper-based alloys, titanium or its alloys, and nickel-based alloys. The thickness of the cannula 626 is preferably in the range from 0.08 mm to 1.0 mm and more preferably in the range from 0.05 mm to 0.4 mm.

As shown in FIGS. 24 and 25A, cannula 626 is covered with an electrically insulating sleeve 608 to protect the patient's body from the electric current. Electrically insulating sleeve 608 may be a coating (e.g., nylon) or heat shrinkable plastic (e.g., fluropolymer or polyester). As shown in FIG. 24A, the proximal portion of the cannula 626 is left exposed to function as the return electrode 624. The length of the return electrode 624, $L_5$ is preferably in the range from 1 mm to 30 mm and more preferably in the range from 2 mm to 20 mm. The spacing between the most distal portion of the return electrode 624 and the plane of the tissue treatment surface 622 of the electrode support member 620, $L_1$ is preferably in the range from 0.5 mm to 30 mm and more preferably in the range from 1 mm to 20 mm. The thickness of the electrically insulating sleeve 608 is preferably in the range from 0.01 mm to 0.5 mm and more preferably in the range from 0.02 mm to 0.2 mm.

In the embodiment shown in FIG. 24, the fluid path is formed in catheter by an inner lumen 627 or annular gap between the return electrode 624 and a second tubular support member 628 within shaft 461. This annular gap may be formed near the perimeter of the shaft 461 as shown in FIG. 11 such that the electrically conducting fluid tends to flow radially inward towards the target site, or it may be formed towards the center of shaft 461 (not shown) so that the fluid flows radially outward. In both of these embodiments, a fluid source (e.g., a bag of fluid elevated above the surgical site or having a pumping device), is coupled to catheter 461 via a fluid supply tube (not shown) that may or may not have a controllable valve.

In an alternative embodiment shown in FIG. 25A, the electrically conducting fluid is delivered from a fluid delivery element (not shown) that is separate from catheter 461. In arthroscopic surgery, for example, the body cavity will be flooded with isotonic saline and the catheter 461 will be introduced into this flooded cavity. Electrically conducting fluid will be continually resupplied to maintain the conduction path between return electrode 624 and electrode terminals 463.

Figure 26:
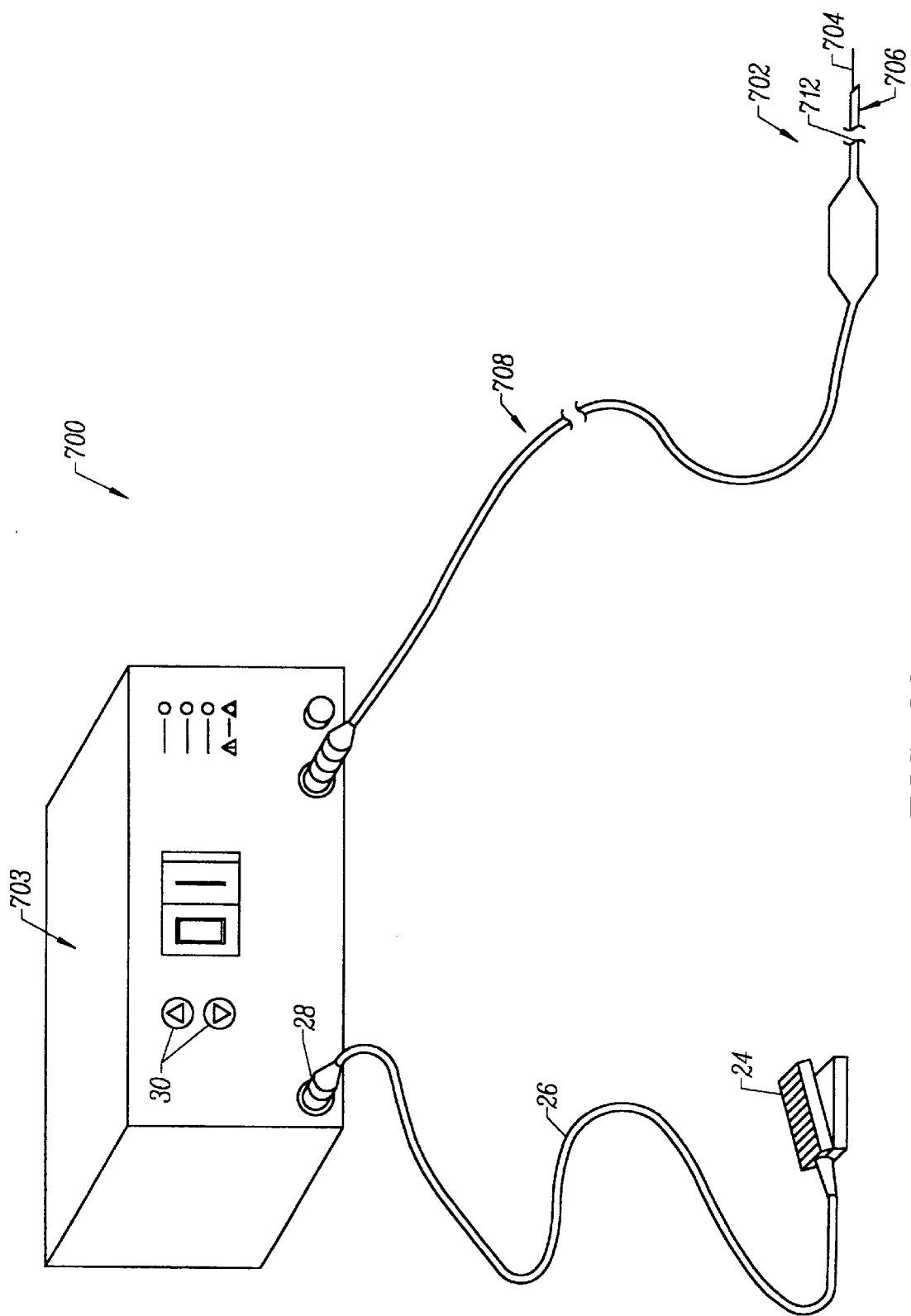
FIG. 26 illustrates an electrosurgical system designed for treating vascular disorders.
Figure 27:
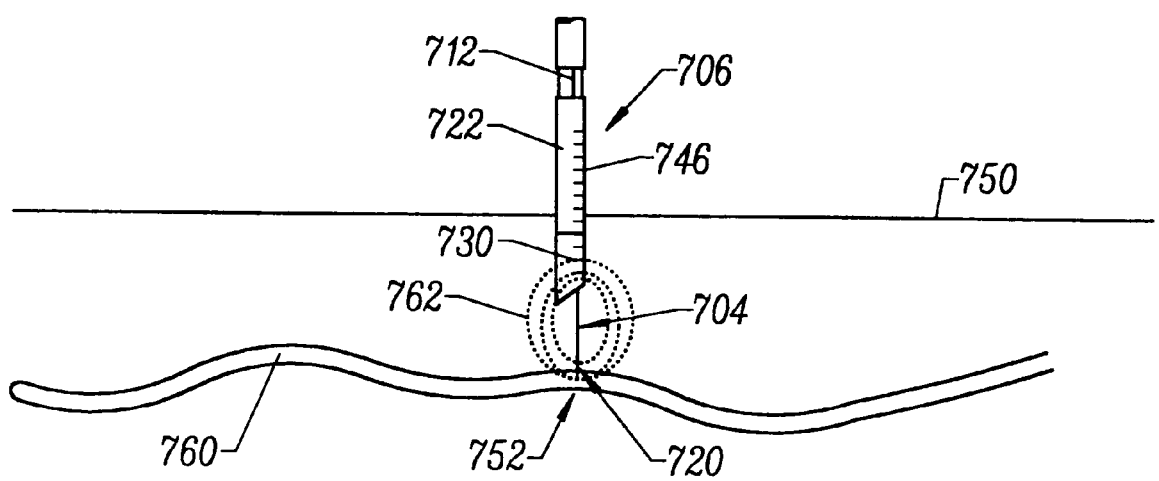
FIG. 27 illustrates a method for treating vascular disorders with the system of FIG. 26.

FIGS. 26 and 27 illustrate a system and method for treating discolored blood vessels, such as cutaneous vascular lesions, port wine stains, face veins, telangiectasis, birth marks, and the like. As shown in FIG. 26, system 700 comprises an electrosurgical assembly 702 connected to a power supply 703 for providing high frequency voltage to a target region of a blood vessel. Electrosurgical assembly generally includes a needle active electrode 704 and a return electrode shaft 706 each electrically connected to power supply 704 by a connecting cable 708. In some embodiments, the system 700 may include one or more fluid supply tube(s) (not shown) coupled to a fluid source and a fluid lumen 712 of return electrode shaft 706 for supplying fluid, such as anesthesia, or isotonic saline, to the target site. In some embodiments, the system 700 may also include an aspiration tube (not shown) coupled to a vacuum source and an inner lumen of return electrode shaft 706 for aspirating fluid, tissue debris and/or blood from the target site.

As shown, active electrode 704 comprises a small, acupuncture-sized needle having a diameter in the range of about 0.05 to 2.0 mm, preferably less about 1.0 mm. In the representative embodiment, needle electrode 704 comprises a conductive material, such as tungsten, gold, copper, aluminum, tantalum, stainless steel, or the like. Electrode 704 includes an electrically insulating shrink wrap (not shown) around the conductive shaft to minimize contact with the electric current and surrounding tissue. An exposed section 720 of the distal portion of the active electrode 704 allows for current flow from the active electrode to the patient's body. Preferably, the exposed portion has a length in the range of about 0.5 mm to about 5 mm.

Return electrode shaft 706 comprises a thin, outer shaft 722 with an inner lumen 712 for receiving active electrode 704 therein. Preferably, active electrode 704 is axially movable relative to shaft 706 to vary the distance between the active and return electrode, thereby adjusting the zone of coagulation and necrosis at the target site. Return electrode shaft 706 preferably comprises a conductive material, such as tungsten, gold, copper, aluminum, tantalum, stainless steel, or the like, with an outer insulating jacket (not shown), similar to active electrode 704. An exposed section 730 located at the distal portion of shaft 706 will allow for current flow from the active electrode 704, through the tissue, to the return electrode shaft 706. Preferably, exposed section 730 of the return electrode shaft 706 will have larger than the exposed section 720 of active electrode 704 to minimize current densities at the return electrode, thereby minimizing tissue heating around the return electrode. In addition, return electrode shaft 706 will preferably have a smooth continuous outer surface for this same purpose. In the representative embodiment, the active and return electrode shafts will comprise the same material to minimize any direct current that may be produced by dissimilar metals.

In the representative embodiment, return electrode shaft 706 includes depth markings 746 to allow the surgeon to precisely position the distal end of the shaft 706 at a particular depth location under the surface of the skin (as discussed in detail below). Alternatively, the active electrode 704, or both the active and return electrodes, may include such depth markings. In another alternative embodiment, system 700 includes a temperature controller (not shown) coupled to one or more temperature sensors at or near the distal end of either, or both, the active or return electrodes 704, 706. The controller adjusts the output voltage of the power supply in response to a temperature set point and the measured temperature value. The temperature sensor may be, for example, a thermocouple, located on the active electrode 704 that measures a temperature at the distal end of the active electrode 704. In this embodiment, the temperature set point will preferably be one that corresponds to a tissue temperature that results in the coagulation of blood, i.e., typically about 70° C. to 100° C., without exceeding this range. This helps to limit thermal injury to surrounding tissue. Alternatively, the temperature sensor may be simply attached to an output to allow the physician to monitor the temperature during the procedure. In this case, the physician may act as the feedback mechanism by either adjusting or interrupting the voltage to control the temperature at the target site.

Referring now to FIG. 27, a method for treating a vascular lesion according to the present invention will now be described. As shown, return electrode shaft 706 is advanced through the outer surface 750 of the patient's skin to a location underlying the epidermis. To minimize trauma caused by the advancement of shaft 706, the shaft will typically be delivered to a location between the target region 752, i.e., the sight of the vascular lesion, and the patient's skin. The active electrode needle 704 will then be advanced deeper to the target region 752, as shown in FIG. 27. In most cases, the lesion will be within about 1 to 10 mm from the surface of the skin, however, the invention may be practiced on deeper vessels. The exact distance between the exposed section 730 of the return electrode shaft 706 and the exposed section 720 of the active electrode 704 at the target region 752 will vary depending on the type, and location of the lesion. If it is desired to minimize the zone or area of necrosis and tissue damage to the patient, the exposed sections of the return and active electrodes will be positioned relatively close to each other, or about 0.05 mm to about 5 mm. If it is desired to increase the zone of necrosis, or to minimize the trauma caused by introduction of the return electrode, this distance may be increased. In alternative embodiments, the return electrode may comprise a dispersive return pad placed on the outer skin of the patient.

Once the return and active electrodes 706, 704 are positioned, a high frequency voltage is applied to these electrodes such that an electric current 762 flows therebetween. The electric current 762 will induce a thermal injury to a target region of the blood vessel 760. The thermal injury causes the vessel 760 to shrink, or to thrombose and collapse, so that blood flow through the vessel is restricted or completely interrupted. Preferably, the vessel 760 is injured with minimal thermal energy being applied to the surrounding tissue, which prevents the tissue discoloration or scarring associated with prior art thermal processes.

The lumen 724 within return electrode shaft 706 may also function as a fluid lumen for delivery of fluid to the target site. In one embodiment, the fluid lumen 724 is coupled to a source of electrically conductive fluid, such as isotonic saline, for delivering the conductive fluid to the target site. The electrically conductive fluid tends to decrease the tissue resistance around the target site, which increases the effectiveness of the device by reducing tissue heating around the target site, and by further confining the electric current to the target, thereby reducing collateral tissue damage. In another embodiment, a local anesthetic is delivered alone, or in combination with a conductive fluid, through fluid lumen 724 to the target region such that the procedure may be performed in the doctor's office under local anesthesia. The present invention may be used in combination with a tumescent technique for delivering a relatively large volume of a very dilute solution of a local anesthetic agent and a vasoconstrictor agent to the target site. The anesthetic and vasconstrictor agents may be diluted in a solution of, for example, electrically conductive fluid.

What is claimed is:

1. A method of treating a discolored blood vessel located in tissue under the surface of the skin comprising:

positioning an active electrode in close proximity to a target region of the blood vessel; and applying high frequency electrical energy to the active electrode, the electrical energy being sufficient to effect coagulation of blood within at least a portion of the target region of the vessel, wherein the positioning step comprises applying sufficient high frequency voltage to the outer surface of the skin to remove a portion of the skin and form a hole to the blood vessel, inserting the active electrode through the hole to a position adjacent the target region of the blood vessel, and applying sufficient high frequency voltage to the active electrode to coagulate blood within the vessel.

2. The method of claim 1 wherein the active electrode is introduced through a percutaneous penetration in the outer surface of the skin, and delivered to a location adjacent to or near the target region of the blood vessel.

3. The method of claim 1 further comprising positioning a return electrode on the outer surface of the skin.

4. The method of claim 1 further comprising inserting a return electrode through the outer surface of the skin to a location near the target region and a distal portion of the active electrode.

5. The method of claim 4 wherein the return electrode comprises a hollow shaft, the method further comprising introducing a fluid through the hollow shaft into the blood vessel.

6. The method of claim 4 further comprising spacing a distal end of the return electrode from an exposed portion of the active electrode by a distance of about 0.05 to about 5.0 mm.

7. The method of claim 5 wherein the fluid comprises an electrically conductive fluid.

8. The method of claim 5 wherein the fluid comprises an anesthetic.

9. The method of claim 4 further comprising varying a distance between a distal portion of the return electrode and an exposed region of the active electrode to control a size of tissue coagulation or necrosis around the blood vessel.

10. The method of claim 1 wherein the blood vessel comprises a vascular lesion.

11. The method of claim 1 further comprising applying sufficient electrical energy to coagulate the target region of the blood vessel without causing permanent thermal injury to the tissue between the skin surface and said region of the blood vessel.

12. An apparatus for treating a discolored blood vessel located in tissue under the surface of the skin comprising:

an instrument having proximal and distal end portions and an active electrode on the distal end portion configured for insertion into an interior of a blood vessel;

a return electrode comprising a hollow shaft having an inner lumen for receiving the active electrode, and a distal end configured for insertion through the outer surface of the skin to a location underneath the skin and outside of the interior the blood vessel; and a high frequency power supply coupled to the active and return electrodes for applying a high frequency voltage difference therebetween, the high frequency voltage difference being sufficient to coagulate a target region of the blood vessel.

13. The apparatus of claim 12 wherein the active electrode comprises a conductive needle having an insulated proximal portion and an exposed distal portion, the needle having a diameter less than about 0.05 to 2.0 mm.

14. The apparatus of claim 13 wherein the exposed distal portion has a length of about 0.5 to about 5.0 mm.

15. The apparatus of claim 12 wherein the hollow shaft has a fluid lumen for delivering an electrically conductive fluid to the target site.

16. The apparatus of claim 12 wherein the active electrode is axially movable relative to the hollow shaft.

17. The apparatus of claim 12 further comprising depth markings on either the instrument or the return electrode for determining a depth of penetration beneath the outer surface of the skin.

* * * * *